(12) United States Patent
Nielsen et al.

(10) Patent No.: US 7,951,556 B2
(45) Date of Patent: May 31, 2011

(54) MUTATED PROKARYOTIC CELLS WITH HIGH SECRETION-LEVELS

(75) Inventors: Allan Kent Nielsen, Soborg (DK); Michael Dolberg Rasmussen, Vallensbaek (DK)

(73) Assignee: Novozymes A/S, Bagsvaerd (DK)

( * ) Notice: Subject to any disclaimer, the term of this patent is extended or adjusted under 35 U.S.C. 154(b) by 904 days.

(21) Appl. No.: 10/593,798

(22) PCT Filed: Apr. 7, 2005

(86) PCT No.: PCT/US2005/000236
§ 371 (c)(1),
(2), (4) Date: Sep. 20, 2006

(87) PCT Pub. No.: WO2005/098003
PCT Pub. Date: Oct. 20, 2005

(65) Prior Publication Data
US 2009/0136995 A1    May 28, 2009

Related U.S. Application Data

(60) Provisional application No. 60/562,396, filed on Apr. 14, 2004.

(30) Foreign Application Priority Data

Apr. 7, 2004   (DK) .................................. 2004 00582

(51) Int. Cl.
*C12P 21/04*   (2006.01)
*C12N 1/21*   (2006.01)
(52) U.S. Cl. ................. 435/69.1; 435/252.3; 435/252.31
(58) Field of Classification Search ........................ None
See application file for complete search history.

(56) References Cited

FOREIGN PATENT DOCUMENTS
WO     WO 9849328     11/1998

OTHER PUBLICATIONS

Bork et al. Predicting functions from protein sequence-where are the bottlenecks? Nature Genetics vol. 18 Apr. 1998.*
Chen et al., Journal of Bacteriology, vol. 175, No. 17, pp. 5428-5437 (1993).
Kanamaru et al., Journal of Bacteriology, vol. 184, No. 1, pp. 43-50 (2002).

* cited by examiner

*Primary Examiner* — Manjunath N Rao
*Assistant Examiner* — Kagnew H Gebreyesus
(74) *Attorney, Agent, or Firm* — Michael W. Krenicky

(57) ABSTRACT

A mutated prokaryotic cell, which secretes higher amounts of at least one heterologous polypeptide of interest and which has a reduced expression-level of YusZ or YusX, or homologues thereof, when compared with an otherwise isogenic but non-mutated cell, and methods for constructing and using such a cell in the production of polypeptides.

22 Claims, 1 Drawing Sheet

MUTATED PROKARYOTIC CELLS WITH HIGH SECRETION-LEVELS

CROSS-REFERENCE TO RELATED APPLICATIONS

Figure 1:
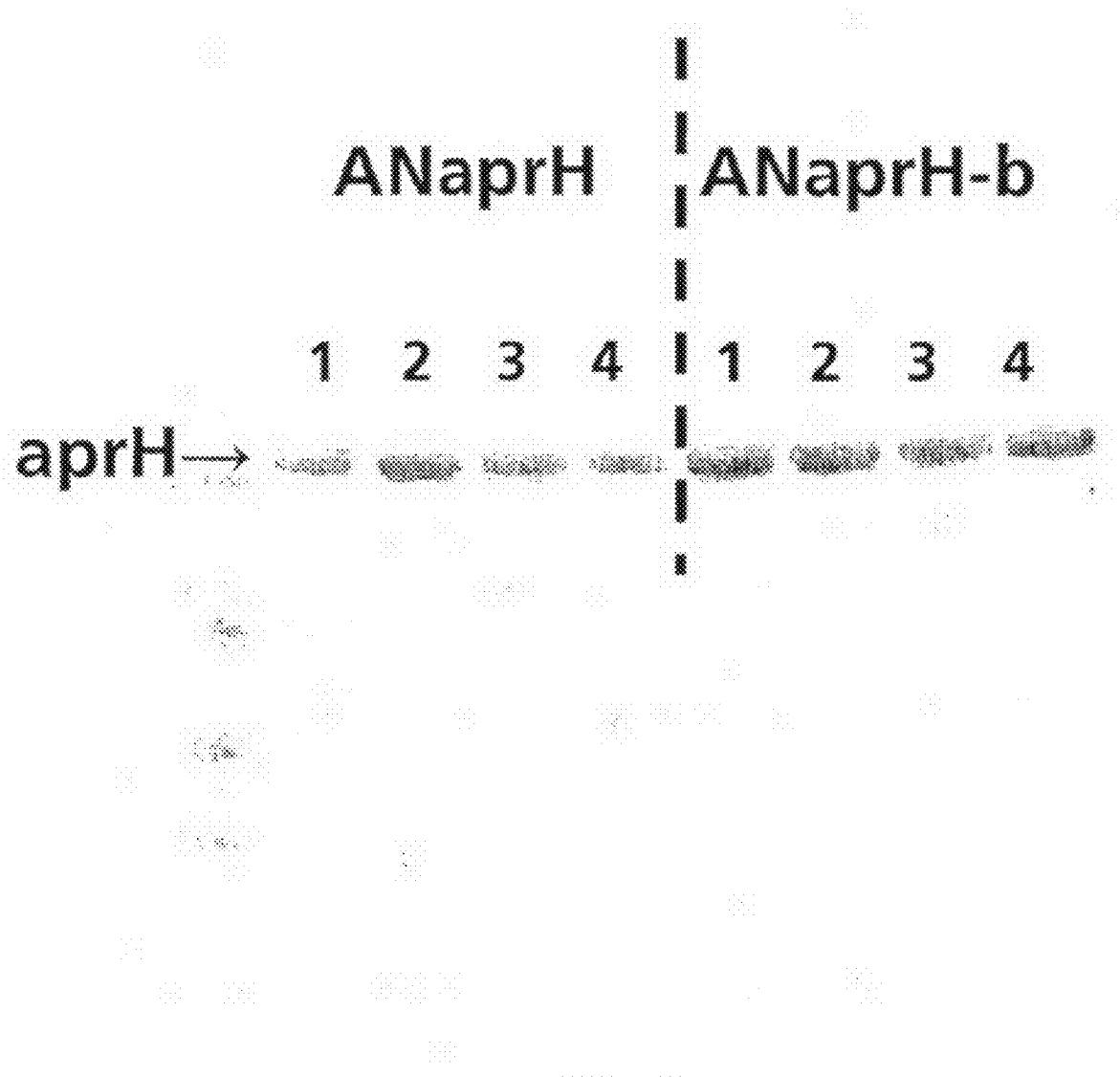

This application is a 35 U.S.C. 371 national application PCT/DK2005/000236, filed Apr. 7, 2005, which claims priority or the benefit under 35 U.S.C. 119 of Danish application no. PA 2004 00582 filed Apr. 7, 2004, and U.S. provisional application no 60/562,396 filed Apr. 14, 2004, the contents of which are fully incorporated herein by reference.

FIELD OF INVENTION

The present invention relates to mutated prokaryotic cells, which secrete higher amounts of at least one heterologous polypeptide of interest and which have a reduced expression-level of YusZ or YusX, or homologues thereof, when compared with otherwise isogenic but non-mutated cells, and methods for constructing and using such cells in the production of polypeptides.

BACKGROUND

The yusZ and yusX DNA sequences were first reported in 1993, but merely as putative open reading frames (Chen et al, 1993, Metalloregulation in *Bacillus subtilis*: isolation and characterization of two genes differentially repressed by metal ions, J Bact 175(17): 5428-5437).

In a later publication it was speculated that yusX, and an open reading frame located immediately upstream of yusX, denoted yusY, could have arisen from a frameshift mutation in a single yusXY gene. However, no further investigation was carried out and the authors of the publication concluded that the function of the gene(s) in the cell remained unknown (Kanamaru et al, 2002, Overexpression of the PepF Oligopeptidase Inhibits Sporulation Initiation in *Bacillus subtilis*, J Bact 184(1): 43-50).

DEFINITIONS

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989") DNA Cloning: A Practical Approach, Volumes I and II/D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984).

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

A "nucleic acid molecule" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization.

For purposes of the present invention, hybridization indicates that the nucleotide sequence hybridizes to a labeled polynucleotide probe which hybridizes to the nucleotide sequence shown in SEQ ID NO:1, SEQ ID NO: 3, or SEQ ID NO: 5 under very low to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is the complementary strand of a fragment of at least 15 nucleotides of SEQ ID NO:1, SEQ ID NO: 3, or SEQ ID NO: 5. In another interesting embodiment, the polynucleotide probe is a fragment of at least 15 nucleotides of the complementary strand of any nucleotide sequence which encodes the polypeptide of SEQ ID NO:2, SEQ ID NO: 4, or SEQ ID NO: 6. In a further interesting embodiment, the polynucleotide probe is the complementary strand of SEQ ID NO:1, SEQ ID NO: 3, or SEQ ID NO: 5. In a still further interesting embodiment, the polynucleotide probe is the complementary strand of the mature polypeptide coding region of SEQ ID NO:1, SEQ ID NO: 3, or SEQ ID NO: 5.

For long probes of at least 100 nucleotides in length, very low to very high stringency conditions are defined as prehybridization and hybridization at 42° C. in 5×SSPE, 1.0% SDS, 5×Denhardt's solution, 100 microg/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 2×SSC, 0.1% SDS at 42° C. (very low stringency), preferably washed three times each for 15 minutes using 0.5×SSC, 0.1% SDS at 42° C. (low stringency), more preferably washed three times each for 15 minutes using 0.2×SSC, 0.1% SDS at 42° C. (medium stringency), even more preferably washed three times each for 15 minutes using 0.2×SSC, 0.1% SDS at 55° C. (medium-high stringency), most preferably washed three times each for 15 minutes using 0.1×SSC, 0.1% SDS at 60° C. (high stringency), in particular washed three times each for 15 minutes using 0.1×SSC, 0.1% SDS at 68° C. (very high stringency).

Although not particularly preferred, it is contemplated that shorter probes, e.g. probes which are from about 15 to 99 nucleotides in length, such as from about 15 to about 70 nucleotides in length, may be also be used. For such short probes, stringency conditions are defined as prehybridization, hybridization, and washing post-hybridization at 5° C. to 10° C. below the calculated Tm using the calculation according to Bolton and McCarthy (1962, Proceedings of the National Academy of Sciences USA 48: 1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated Tm.

A DNA "coding sequence" or an "open reading frame (ORF)" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

An expression vector is a DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "secretory signal sequence" is a DNA sequence that encodes a polypeptide (a "secretory peptide" that, as a component of a larger polypeptide, directs the larger polypeptide through a secretory pathway of a cell in which it is synthesized. The larger polypeptide is commonly cleaved to remove the secretory peptide during transit through the secretory pathway.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A chromosomal gene is rendered non-functional if the polypeptide that the gene encodes can no longer be expressed in a functional form. Such non-functionality of a gene can be induced by a wide variety of genetic manipulations as known in the art, some of which are described in Sambrook et al. vide supra. Partial deletions within the ORF of a gene will often render the gene non-functional, as will mutations.

The term "an expressible copy of a chromosomal gene" is used herein as meaning a copy of the ORF of a chromosomal gene, wherein the ORF can be expressed to produce a fully functional gene product. The expressible copy may not be transcribed from the native promoter of the chromosomal gene, it may instead be transcribed from a foreign or heterologous promoter, or it may indeed be promoterless and expressed only by transcriptional read-through from a gene present upstream of the 5' end of the ORF. Transcriptional read-through is intended to have the same meaning here as the generally recognized meaning in the art.

"Operably linked", when referring to DNA segments, indicates that the segments are arranged so that they function in concert for their intended purposes, e.g. transcription initiates in the promoter and proceeds through the coding segment to the terminator.

A coding sequence is "under the control" of transcriptional and translational control sequences in a cell when RNA polymerase transcribes the coding sequence into mRNA, which is then trans-RNA spliced and translated into the protein encoded by the coding sequence.

"Heterologous" DNA refers to DNA not naturally located in the cell, or in a chromosomal site of the cell. Preferably, the heterologous DNA includes a gene foreign to the cell.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a polypeptide of interest. The construct may optionally contain other nucleic acid segments.

The nucleic acid construct of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., supra).

The nucleic acid construct of the invention encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques. The nucleic acid construct may also be prepared by polymerase chain reaction using specific primers, for instance as described in U.S. Pat. No. 4,683,202 or Saiki et al., Science 239 (1988), 487-491.

The term nucleic acid construct may be synonymous with the term "expression cassette" when the nucleic acid construct contains the control sequences necessary for expression of a coding sequence of the present invention The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcription and translation control sequences which mediate the expression of the polypeptide. The promoter may be any nucleic acid sequence which shows transcriptional activity in the host cell of choice and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the expressed polypeptide into the cell's secretory pathway of the host cell. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. A foreign signal peptide coding region may be required where the coding sequence does not normally contain a signal peptide coding region. Alternatively, the foreign signal peptide coding region may simply replace the natural signal peptide coding region in order to obtain enhanced secretion of the exoprotein relative to the natural signal peptide coding region normally associated with the coding sequence. The signal peptide coding region may be obtained from a glucoamylase or an amylase gene from an *Aspergillus* species, a lipase or proteinase gene from a *Rhizomucor* species, the gene for the alpha-factor from *Saccharomyces cerevisiae*, an amylase or a protease gene from a *Bacillus* species, or the calf preprochymosin gene. However, any signal peptide coding region capable of directing the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems.

Examples of suitable promoters for directing the transcription of the gene(s) of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus subtilis* alkaline protease gene, the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus amyloliquefaciens* BAN amylase gene, the *Bacillus licheniformis* penicillinase gene (penP), the *Bacillus subtilis* xylA and xylB genes, and the prokaryotic beta-lactamase gene (Villa-Kamaroff et al., 1978, Proceedings of the National Academy of Sciences USA 75:3727-3731), as well as the tac promoter (DeBoer et al., 1983, Proceedings of the National Academy of Sciences USA 80:21-25). Further promoters are described in "Useful proteins from recombinant bacteria" in Scientific American, 1980, 242:74-94; and in Sambrook et al., 1989, supra.

An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* PrsA gene. Further signal peptides are described by Simonen and Palva, 1993, Microbiological Reviews 57:109-137.

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Antibiotic selectable markers confer antibiotic resistance to such antibiotics as ampicillin, kanamycin, chloramphenicol, tetracycline, neomycin, hygromycin or methotrexate. Suitable markers for yeast host cells are ADE2, HIS3, LEU2, LYS2, MET3, TRP1, and URA3.

The vectors of the present invention preferably contain an element(s) that permits stable integration of the vector, or of a smaller part of the vector, into the host cell genome or autonomous replication of the vector in the cell independent of the genome of the cell.

The vectors, or smaller parts of the vectors such as amplification units of the present invention, may be integrated into the host cell genome when introduced into a host cell. For chromosomal integration, the vector may rely on the nucleic acid sequence encoding the polypeptide or any other element of the vector for stable integration of the vector into the genome by homologous or nonhomologous recombination.

Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences; specific examples of encoding sequences suitable for site-specific integration by homologous recombination are given in WO 02/00907 (Novozymes, Denmark), which is hereby incorporated by reference in its totality.

On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences. The copy number of a vector, an expression cassette, an amplification unit, a gene or indeed any defined nucleotide sequence is the number of identical copies that are present in a host cell at any time. A gene or another defined chromosomal nucleotide sequence may be present in one, two, or more copies on the chromosome. An autonomously replicating vector may be present in one, or several hundred copies per host cell.

An amplification unit of the invention is a nucleotide sequence that can integrate into the chromosome of a host cell, whereupon it can increase in number of chromosomally integrated copies by duplication of multiplication. The unit comprises an expression cassette as defined herein comprising at least one copy of a gene of interest and an expressable copy of a chromosomal gene, as defined herein, of the host cell. When the amplification unit is integrated into the chromosome of a host cell, it is defined as that particular region of the chromosome which is prone to being duplicated by homologous recombination between two directly repeated regions of DNA. The precise border of the amplification unit with respect to the flanking DNA is thus defined functionally, since the duplication process may indeed duplicate parts of the DNA which was introduced into the chromosome as well as parts of the endogenous chromosome itself, depending on the exact site of recombination within the repeated regions. This principle is illustrated in Janniere et al. (1985, Stable gene amplification in the chromosome of *Bacillus subtilis*. Gene, 40: 47-55), which is incorporated herein by reference.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMbeta1. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, Proceedings of the National Academy of Sciences USA 75:1433).

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The transformation of a bacterial host cell may, for instance, be effected by protoplast transformation (see, e.g., Chang and Cohen, 1979, Molecular General Genetics 168: 111-115), by using competent cells (see, e.g., Young and Spizizin, 1961, Journal of Bacteriology 81:823-829, or Dubnar and Davidoff-Abelson, 1971, Journal of Molecular Biology 56:209-221), by electroporation (see, e.g., Shigekawa and Dower, 1988, Biotechniques 6:742-751), or by conjugation (see, e.g., Koehler and Thorne, 1987, Journal of Bacteriology 169:5771-5278).

The transformed or transfected host cells described above are cultured in a suitable nutrient medium under conditions permitting the expression of the desired polypeptide, after which the resulting polypeptide is recovered from the cells, or the culture broth.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art (see, e.g., references for bacteria and yeast; Bennett, J. W. and LaSure, L., editors, More Gene Manipulations in Fungi, Academic Press, CA, 1991).

The polypeptide are recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989).

In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

In the present context, the homology between two amino acid sequences or between two nucleotide sequences is described by the parameter "identity". For purposes of the present invention, alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Multiple alignments of protein sequences may be made using "ClustalW" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680). Multiple alignment of DNA sequences may be done using the protein alignment as a template, replacing the amino acids with the corresponding codon from the DNA sequence.

In the present context, a functional homologue of the YusZ or YusX protein is a protein, which when expressed at a reduced level in a cell, leads to an increased secretion of a heterologous polypeptide, preferably an enzyme such as an alpha-amylase, when compared with an isogenic cell having a normal expression of the YusZ or YusX functional homologue, where both are cultivated under essentially identical conditions. In addition, the functional homologue of the YusZ or YusX protein shares an amino acid sequence identity with the respective YusZ or Yus X protein of at least 50%, preferably 55%, 60%, 65%, 70%, 75%, 80%, 85%, 90%, 95%, 97%, or most preferably 99% when aligned as described above.

In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. Allelic variants are included in the present definition of functional homologues.

The YusZ or YusX protein or functional homologue thereof may be a wild-type protein identified and isolated from a natural source. Such wild-type proteins may be specifically screened for by standard techniques known in the art. Furthermore, genes encoding the YusZ or YusX protein, or a functional homologue thereof, may be prepared by the DNA shuffling technique, such as described in J. E. Ness et al. Nature Biotechnology 17, 893-896 (1999). Moreover, the YusZ or YusX protein, or functional homologue thereof, may be an artificial variant. Such artificial variants may be constructed by standard techniques known in the art, such as by site-directed/random mutagenesis. In one embodiment of the invention, amino acid changes (in the artificial variant as well as in wild-type polypeptides) are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. For a general description of nucleotide substitution, see, e.g., Ford et al., 1991, Protein Expression and Purification 2: 95-107.

FIGURES

FIG. 1 shows a stained or labeled Poly Acrylamid Gel Electrophoresis (PAGE) gel as described in example 7 below. The yield of protease from a yusZ-deletion strain denoted ANaprH-b was determined from four independent isolates (FIG. 1, No's 1-4) and compared to the yield of protease from four independent isolates of the otherwise isogenic control strain ANaprH by PAGE. It is clear from the difference in the thickness of the labeled protease bands on the PAGE gel, that the yusZ-deleted strain (ANaprH-b) produces more protease than the corresponding reference strain (ANaprH).

SUMMARY OF THE INVENTION

The *Bacillus subtilis* yusZ DNA sequence is shown in SEQ ID NO: 1, the putative encoded amino acid sequence is shown in SEQ ID NO: 2, the *B. subtilis* yusX DNA sequence is shown in SEQ ID NO: 3, and the putative encoded amino acid sequence is shown in SEQ ID NO: 4; the *B. subtilis* yusY DNA sequence is shown in SEQ ID NO: 5, and the putative encoded amino acid sequence is shown in SEQ ID NO: 6. The *Bacillus licheniformis* yusZ DNA sequence is shown in SEQ ID NO: 24, the putative encoded amino acid sequence is shown in SEQ ID NO: 25.

A problem to be solved is how to provide increased secretion of heterologous polypeptides produced in prokaryotic cells. The present invention provides mutated prokaryotic cells which have a reduced expression-level of YusZ (SEQ ID NO's: 2 or 25), YusX (SEQ ID NO: 4), or homologues thereof, and which secrete higher amounts of at least one heterologous polypeptide of interest, when compared with respective corresponding otherwise isogenic but non-mutated cells. Typically, a mutated cell of the invention is compared under identical growth conditions with the non-mutated parent cell from which the mutant was derived; the parent cell will be completely isogenic with the mutated cell, except for the mutations leading to the reduced YusZ or YusX expression-levels. The inventors have found that a reduced expression-level of YusZ or YusX in a prokaryotic host cell leads to a higher yield of secreted heterologous polypeptides. This result is highly interesting for the industrial production of secreted polypeptides such as enzymes.

Accordingly, in a first aspect the invention relates to a mutated prokaryotic cell, which has a reduced expression-level of YusZ (SEQ ID NO's: 2 or 25), YusX (SEQ ID NO: 4), or homologues thereof, and which secretes higher amounts of at least one heterologous polypeptide of interest, when compared with an otherwise isogenic but non-mutated cell.

In a second aspect the invention relates to a method for constructing a mutated prokaryotic cell, said method comprising the steps of:
 a) mutating a prokaryotic cell; and
 b) selecting a mutated cell which has a reduced expression-level of YusZ (SEQ ID NO's: 2 or 25) or YusX (SEQ ID NO: 4), or homologues thereof, and which secretes higher amounts of at least one heterologous polypeptide of interest, when compared with an otherwise isogenic but non-mutated cell.

A final aspect of the invention relates to a method for producing a polypeptide of interest, said method comprising the steps of:
 a) cultivating a mutated prokaryotic cell, which has a reduced expression-level of YusZ (SEQ ID NO's: 2 or 25), YusX (SEQ ID NO: 4), or homologues thereof, and which secretes higher amounts of the polypeptide of interest, when compared with an otherwise isogenic but non-mutated cell; and
 b) isolating the polypeptide of interest.

DETAILED DESCRIPTION

The first aspect of the invention relates to a mutated prokaryotic cell, which has a reduced expression-level of YusZ (SEQ ID NO's: 2 or 25), YusX (SEQ ID NO: 4), or homologues thereof, and which secretes higher amounts of at least one heterologous polypeptide of interest, when compared with an otherwise isogenic but non-mutated cell.

A preferred embodiment of the invention relates to a cell of the first aspect, which is a Gram-positive cell, preferably a *Bacillus* cell, more preferably a *B. alkalophilus, B. amyloliquefaciens, B. brevis, B. circulans, B. clausii, B. coagulans, B. lautus, B. lentus, B. licheniformis, B. megaterium, B. stearothermophilus, B. subtilis*, or *B. thuringiensis* cell; or to methods of the second or third aspects, wherein the cell is as listed here.

An evolutionary homologue of the YusZ or YusX protein, an allellic variant, an artificial variant, a shuffled protein, a species variant, and so forth, are all referred to as a "functional homologue" or the YusZ or YusX protein in the present description, and the inventors envision that reduced expression of such functional homologue protein(s) will be equally effective in the cell and methods of the invention.

Specifically, a preferred embodiment relates to the cell, wherein the YusZ or YusX protein or functional homologue thereof comprises an amino acid sequence which is at least 70% identical to the amino sequence shown in SEQ ID NO:2 or SEQ ID NO: 4, respectively; preferably at least 75%, 80%, 85%, 90%, 95%, 97%, or even 99% identical to the amino sequence shown in SEQ ID NO:2 or SEQ ID NO: 4, respectively.

Another preferred embodiment relates to the cell of the invention, or the methods of the invention, wherein the YusZ or YusX protein or functional homologue thereof comprises or consists of the amino acid sequence shown in SEQ ID NO:2 or SEQ ID NO:4, respectively.

Due to the organisation of the yusX and yusY genes in an operon, reduced expression of YusX may be achieved by mutating the encoding gene, or by mutating the immediately upstream open reading frame of the operon, yusY.

Accordingly, in a preferred embodiment of the invention, the reduced expression of YusZ or YusX or homologues thereof is achieved by mutating one or more respective encoding gene, a cell of the invention is preferably mutated in yusZ (SEQ ID NO's: 1 or 24), yusX (SEQ ID NO: 3), and/or yusY (SEQ ID NO: 5), or homologues thereof; and preferably the yusZ, yusX, and/or yusY homologues encode a polypeptide having an amino acid sequence at least 70% identical to the sequence shown in SEQ ID NO's: 2 or 25, SEQ ID NO: 4, or SEQ ID NO: 6, respectively; or preferably at least 75%, 80%, 85%, 90%, 95%, 97%, or even 99% identical to the amino sequence shown in SEQ ID NO:2, SEQ ID NO: 4, or SEQ ID NO: 6, respectively; most preferably, the yusZ, yusX, and/or yusY homologues have a nucleotide sequence at least 70% identical to the sequence shown in SEQ ID NO's: 1 or 24, SEQ ID NO: 3, or SEQ ID NO: 5, respectively; or preferably at least 75%, 80%, 85%, 90%, 95%, 97%, or even 99% identical to the sequence shown in SEQ ID NO's: 1 or 24, SEQ ID NO: 3, or SEQ ID NO: 5, respectively.

As mentioned elsewhere herein, one way of identifying functional yusZ, yusX, or YusY genes in a cell is by hybridization. Accordingly, a preferred embodiment relates to a cell of the first aspect, or methods of the second or third aspects wherein the cell is mutated in at least one polynucleotide, where a subsequence having a size of at least 100 bp of the at least one polynucleotide hybridizes with a polynucleotide having the sequence shown in SEQ ID NO's: 1 or 24, SEQ ID NO: 3, or SEQ ID NO: 5, or the respective complementary sequences, under very low to very high stringency conditions, preferably very low, low, medium, medium-high, high, or very high stringency hybridization conditions.

The cell of the present invention may be mutated in any suitable manner and procedures for performing such mutagenesis are very well-known in the art.

A preferred embodiment of the invention relates to a cell of the first aspect, in which yusZ, yusX, and/or yusY, or homologues thereof, is/are partially or fully deleted from the chromosome.

Another preferred embodiment relates to a cell, in which yusZ, yusX, and/or yusY, or homologues thereof, comprise at least one frameshift mutation or non-sense mutation.

The mutated cell of the invention has a reduced expression-level of YusZ or YusX protein or a functional homologue thereof, than an otherwise isogenic but non-mutated cell, e.g. a parent cell. A comparison should be made by cultivating the cell of the invention as well as the isogenic but non-mutated cell under essentially identical conditions, and comparing the amount of YusZ or YusX protein by any standard method in the art. Preferably the cell of the invention produces at least 5% less YusZ or YusX than the non-mutated cell, more preferably at least 10%, still more preferably at least 20%, and most preferably at least 50% less YusZ or YusX protein or a functional homologue thereof.

In a preferred embodiment, the cell of the invention has at least a two-fold reduced expression-level of YusZ or YusX, or homologues thereof, when compared with the otherwise isogenic but non-mutated cell; preferably the cell has no measurable expression of YusZ or YusX, or homologues thereof, when compared with the otherwise isogenic but non-mutated cell.

As the inventors show herein, a cell of the first aspect is capable of secreting greater amounts of a heterologous polypeptide of interest than the corresponding isogenic but non-mutated cell, when both are cultivated under essentially identical conditions.

Accordingly, a preferred embodiment of the invention relates to the cell of the first aspect, which secretes greater amounts of a heterologous polypeptide of interest than an otherwise isogenic but non-mutated cell. Preferably the cell of the invention secretes at least 5% more, more preferably at least 10% more, still more preferably at least 20% more, and most preferably at least 50% more than the non-mutated cell. The amount of secreted heterologous polypeptide from the cell may be determined by any suitable assay in the art; a non-limiting example is shown below with the determination of secreted amounts of alpha-amylase.

In a preferred embodiment of the invention, the at least one heterologous polypeptide comprises an enzyme, preferably the enzyme is a lyase, a ligase, a hydrolase, an oxidoreductase, a transferase, or an isomerase.

Methods of stably integrating one or more copies of polynucleotides encoding heterologous polypeptides into the chromosome of prokaryotic cells are well described in the art, for instance in WO 94/14968, WO 99/41358, WO 91/09129, WO 02/00907, or WO 01/90393, which are all incorporated herein by reference in their entirety.

Accordingly, in a preferred embodiment of the invention, the cell comprises one or more chromosomally integrated copies of a polynucleotide encoding the at least one heterologous polypeptide.

The skilled person is well aware that increased expression of the polynucleotide encoding the polypeptide of interest is advantageous in the industrial production of polypeptides, and it is common knowledge in the art that increasing promoter strength is one way of achieving increased expression, see WO 99/43835, WO 93/10249, WO 98/07846, or WO 03/008575, which are incorporated herein by reference in their entirety.

A preferred embodiment relates to the cell of the invention, wherein the at least one heterologous polypeptide is encoded by a polynucleotide which is transcribed from at least one heterologous promoter, preferably the at least one promoter comprises an artificial promoter, and more preferably the artificial promoter comprises one or more mRNA-stabilizing sequence, preferably derived from the cryIIIa promoter.

EXAMPLES

Materials and methods

Strains

*B. subtilis* 168. F. Kunst et. al. "The complete genome sequence of the Gram-positive bacterium *Bacillus subtilis*" *Nature* (1997) 390:249-256.

*B. subtilis* AN83. This strain is the *B. subtilis* 168 with the plasmid pKTH10 which constitutively expresses an amylase in high amounts.

*B. subtilis* AN133. This strain is the *B. subtilis* 168 strain wherein the yusZ gene is deleted.

*B. subtilis* AN137. This strain is AN133 with the plasmid pKTH10 which constitutively expresses an amylase in high amounts.

*B. subtilis* AN151. This strain is the *B. subtilis* 168 strain wherein the yusX gene is deleted

*B. subtilis* AN155. This strain is AN151 with the plasmid pKTH10 which constitutively expresses an amylase in high amounts.

*B. licheniformis* SJ1707. This strain is described in U.S. Pat. No. 5,698,415.

*B. licheniformis* AN10R. This strain is SJ1707 engineered to overexpress protease 10R from *Nocardiopsis prasina* NRLL 18262 (WO 1988/003947).

*B. licheniformis* AN10R-b. This strain is the *B. licheniformis* AN10R strain wherein the yusZ gene is deleted.

*B. licheniformis* ANaprH. This strain is SJ1707 engineered to overexpress the aprH alkaline protease gene from *Bacillus clausii*.

*B. licheniformis* ANaprH-b. This strain is the *B. licheniformis* ANaprH strain wherein the yusZ gene is deleted.

*B. subtilis* PP289-5. The donor strain for conjugative transfer of plasmids containing oriT from pUB110 (described in WO96/23073).

*B. subtilis* AN220. This strain is *B. subtilis* 168 engineered to overexpress the apr alkaline protease gene from *Bacillus amyloliquefaciens*.

*B. subtilis* AN225. This strain is AN220 wherein the yusZ gene is deleted.

Primers:

Plasmids pKTH10: Vehmaanpera J, Steinborn G, Hofemeister J.: "Genetic manipulation of *Bacillus amyloliquefaciens*." J. Biotechnol. 1991 July; 19(2-3):221-40. This plasmid constitutively express the *B. amyloliquefaciens* alpha-amylase (AmyQ).

pSJ6410: a derivative of plasmid pSJ2739 (described in U.S. Pat. No. 6,100,063), which is again derived from pE194, naturally temperature-sensitive for replication. pSJ6410 consists of the pE194 replicon, as well as a fragment derived from plasmid pUB110 and a *Bacillus licheniformis* alpha-amylase gene preceded by a fragment from the *Bacillus thuringiensis* cryIIIA regulatory region. These additional fragments are irrelevant for the use of pSJ6410 as a vector in the present invention.

pAN28: constructed by ligating the PCR product yusz-SOEpcr (SEQ ID NO: 15), cut with restriction enzymes XmaI and KpnI, to the large XmaI-KpnI fragment of pSJ6410. This plasmid, which contains the temperature sensitive origin of pE194, was used for deletion of the yusZ gene from the chromosome of *B. subtilis* 168 by a double cross-over event. The PCR product yuszSOEpcr was generated by use of the technique of splicing by overlap extension by the polymerase chain reaction (SOE by PCR, Horton R M et. al. Biotechniques. 1990 May; 8(5):528-35). Two intermediate PCR products, PCR1 and PCR2, each tipped with a small sequence of the other, were mixed in a second-stage PCR to produce the final spliced product, yuszSOEpcr. PCR1, generated by use of primers yusZ1F and yusZ2R, contains yusZ upstream sequence (655 bp). PCR2, generated by use of primers yusZ2F and yusZ3R, contains yusZ downstream sequence (690 bp). Chromosomal DNA from *B. subtilis* 168 was used as a template for PCR. The spliced product (1315 bp), wherein the yusZ gene is reduced from encoding 280aa to encode only 25aa, was generated in the second-stage PCR using PCR1 and PCR2 as templates, and yusZ1F and yusZ3R as primers. The entire nucleotide sequence of plasmid pAN28 is shown in SEQ ID NO: 16.

pAN23: constructed by ligating the PCR product yusx-SOEpcr (SEQ ID NO: 17), cut with restriction enzymes XmaI and KpnI, to the large XmaI-KpnI fragment of pSJ6410. This plasmid, which contains the temperature sensitive origin of pE194, was used for deletion of the yusX gene from the chromosome of *B. subtilis* 168 by a double cross-over event. The PCR product yusxSOEpcr was generated by use of the technique of splicing by overlap extension by the polymerase chain reaction (SOE by PCR, Horton R M et. al. Biotechniques. 1990 May; 8(5):528-35). Two intermediate PCR products, PCR1 and PCR2, each tipped with a small sequence of the other, were mixed in a second-stage PCR to produce the final spliced product, yusxSOEpcr. PCR1, generated by use of primers yusX1F and yusX2R, contains yusX upstream sequence (560 bp). PCR2, generated by use of primers yusX2F and yusX3R, contains yusX downstream sequence (560 bp). Chromosomal DNA from *B. subtilis* 168 was used

```
yusZ1F     (SEQ ID NO:  7):   ccttcccggggctaagcttttcggc
yusZ2R     (SEQ ID NO:  8):   gatagactcccacgcgctggacgctcctgt
yusZ2F     (SEQ ID NO:  9):   acaggagcgtccagcgcgtgggagtctatc
yusZ3R     (SEQ ID NO: 10):   aacggtaccctgaccaagcagacag
yusX1F     (SEQ ID NO: 11):   aatgcccgggcaagctttacagctg
yusX2R     (SEQ ID NO: 12):   ggcgtcacgcacagcaacgagcgacgattg
yusX2F     (SEQ ID NO: 13):   caatcgtcgctcgttgctgtgcgtgacgcc
yusX3R     (SEQ ID NO: 14):   aatcggtaccatcataatgactgtc
yusZlich1F (SEQ ID NO: 19):   tcagcagcccgcggagcagccgttttaatggaacc
yusZlich2R (SEQ ID NO: 20):   atgaccgcacgttcccaaatgctcgtcgcgcccgttacaa
yusZlich3F (SEQ ID NO: 21):   ttgtaacgggcgcgacgagcatttgggaacgtgcggtcat
yusZlich4R (SEQ ID NO: 22):   gcggatttgacgtcaatcgcttaccagtgcggaaac
``` as a template for the PCR. The spliced product (1090 bp), wherein the yusX gene is reduced from 500aa to 27aa, was generated in the second-stage PCR using PCR1 and PCR2 as templates, and yusX1F and yusX3R as primers. The entire sequence of plasmid pAN23 is shown in SEQ ID NO: 18.

pAN212b: a derivative of plasmid pSJ2739 (described in U.S. Pat. No. 6,100,063) which in turn was derived from plasmid pE194, a naturally temperature-sensitive plasmid for replication. pAN212b consists of the pE194 replicon, as well as a fragment derived from plasmid pUB110. The entire sequence of plasmid pAN212b is shown in SEQ ID NO: 23.

General Molecular Biology Methods

Unless otherwise mentioned, the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990).

Enzymes for DNA manipulations were used according to the specifications of the suppliers (e.g. restriction endonucleases, ligases etc. are obtainable from New England Biolabs, Inc.).

Competent cells were prepared and transformed as described by Yasbin, R. E., Wilson, G. A. and Young, F. E. (1975) Transformation and transfection in lysogenic strains of *Bacillus subtilis*: evidence for selective induction of prophage in competent cells. J. Bacteriol, 121:296-304.

Media

LB agar: as described in Ausubel, F. M. et al. (eds.) "Current protocols in Molecular Biology". John Wiley and Sons, 1995).

LBP: LB agar supplemented with 0.05 M potassium phosphate, pH 7.0

LBPG: is LB agar supplemented with 0.5% Glucose and 0.05 M potassium phosphate, pH 7.0.

LBPSK: is LB agar supplemented with 0.05 M potassium phosphate, pH 7.0 and 1% of skimmed milk.

BPX: as described in EP 0 506 780 (WO 91/09129).

Fermentations.

Fermentations to evaluate the amylase yields were performed in shakeflasks with 100 ml BPX at 37° C., 300 rpm for seven days. Culture volumes of 10 ml were harvested and centrifuged at 10.000 g to remove cells and debris. The clear supernants were used for assaying alpha-amylase activity.

Assay for Alpha-amylase Activity

Alpha-amylase activity was determined by a method employing an enzymatic calorimetric test with 4,6-ethylidene ($G_7$)-p-nitrophenyl($G_1$)-a,D-maltoheptaoside (ethylidene-$G_7$PNP) as substrate (Boehringer Mannheim, Germany art. 1442309). Under a specified set of conditions (temp., pH, reaction time, buffer conditions) 1 mg of a given a-amylase will hydrolyse a certain amount of substrate and a yellow colour will be produced. The colour intensity is measured at 405 nm. The measured absorbance is directly proportional to the activity the a-amylase in question under a given set of conditions.

Protease Assay

Protease activity was measured spectrophotometrically in microtiterplates. Proteolytic cleavage of the oligopeptide N-suc-ala-ala-pro-phe-pNA (L-1400, Bachem) develops a yellow colour which can be measured at 405 nm.

Example 1

Construction of a *Bacillus subtilis* yusZ-deletion Mutant

The 1315 bp yuszSOEpcr DNA fragment, which contains an in-frame 255 aa deletion of the yusZ gene, was generated by SOE by PCR, and cloned in a plasmid with a temperature sensitive origin (pSJ6410), resulting in plasmid pAN28. pAN28 was introduced by transformation into the *B. subtilis* 168 strain and plated at 45° C. (non-permissive temperature) on LBPG media supplemented with 1 micro-g/ml erm to select for integrants. Transformants on these plates have integrated the plasmid in the yusZ-upstream or yusZ-downstream locus by a single (erm$^+$) cross-over event. Excision of the plasmid is by either of two ways, which in one case will result in the wildtype strain, and in the other case will result in a strain with the yusZ gene substituted by the yuszSOEpcr (ΔyusZ).

To allow for excision, selection and identification of strains deleted for yusZ, integrants were inoculated in 10 ml of LB and grown overnight at 30° C. (permissive temperature). 100 micro-l of outgrown culture of integrants were transferred to 10 ml of LB and grown at 30° C. for another overnight. Cells were plated on LBPG at 30° C. and strains where double cross-over events occurred (integration-excision) were scored as erm$^-$ by replica plating.

PCR with primers yusZ1F and yusZ3R was performed on strains to determine presence of either a wildtype (2155 bp) or a deleted (1315 bp) yusZ gene in strains where double cross-over events had occurred. A yusZ-deleted strain was isolated and named AN133, and the deletion was verified by a comprehensive sequence analysis which covered the whole yusz-SOEpcr region (primers yusZ1F and yusZ3R).

Example 2

Amylase Yield from *B. subtilis* yusZ-deletion Mutants

AN133 was transformed with plasmid pKTH10 which constitutively expresses the alpha-amylase AmyQ from *Bacillus amyloliquefaciens*. The resulting strain was named AN137. The yield of amylase from AN137 was determined in triplicate from two independent isolates and compared to the yield of amylase from the control strain AN83. The AN137 strain (ΔyusZ) had an increased alpha-amylase yield, which on average is 205% higher than the control strain AN83, which carries the wild-type yusZ gene. Results are shown in table 1.

TABLE 1

Yields of amylase from the AN137 strain (ΔyusZ), and the control strain AN83.

| Strain | Amylase activity (relative) | Average yields | Average yields |
|---|---|---|---|
| AN137-1.1 | 21.5 | 19.3 | 205% |
| AN137-1.2 | 20.3 | | |
| AN137-1.3 | 18.1 | | |
| AN137-2.1 | 17.4 | | |
| AN137-2.2 | 20.6 | | |
| AN137-2.3 | 17.8 | | |
| AN83-1.1 | 9.11 | 9.4 | 100% |
| AN83-1.2 | 7.52 | | |
| AN83-1.3 | 6.76 | | |
| AN83-2.1 | 10.5 | | |

TABLE 1-continued

Yields of amylase from the AN137 strain (ΔyusZ), and the control strain AN83.

| Strain | Amylase activity (relative) | Average yields | Average yields |
|---|---|---|---|
| AN83-2.2 | 10.5 | | |
| AN83-2.3 | 11.9 | | |

Example 3

Construction of a *B. subtilis* yusX-deletion Mutant

The 1090 bp yusxSOEpcr DNA fragment, which contains an in-frame 473 aa deletion of the yusX gene, was generated by SOE by PCR, and cloned in a plasmid with a temperature sensitive origin (pSJ6410), resulting in plasmid pAN23, as described above. pAN23 was introduced by transformation into the *B. subtilis* 168 strain and plated at 45° C. (non-permissive temperature) on LBPG media supplemented with 1 micro-g/ml erm to select for integrants. Transformants on these plates have integrated the plasmid in the yusX-upstream or yusX-downstream locus by a single (erm+) cross-over event. Excision of the plasmid is by either of two ways, which in one case will result in the wildtype strain, and in the other case will result in a strain with the yusX gene substituted by the yusxSOEpcr (ΔyusX).

To allow for excision, selection and identification of strains deleted for yusX, integrants were inoculated in 10 ml of LB and grown overnight at 30° C. (permissive temperature). 100 microliter of outgrown culture of integrants were transferred to 10 ml of LB and grown at 30° C. for another overnight. Cells were plated on LBPG at 30° C. and strains where double cross-over events occurred (integration-excision) were scored as erm− by replica plating. PCR with primers yusX1F and yusX3R were performed on strains to determine presence of wt- (2539 bp PCR-product) or truncated- (1090-bp PCR-product) yusX gene in strains where double cross-over events occurred. A yusX-deleted strain was named AN151 and verified by a comprehensive sequence analysis which covered the whole yusxSOEpcr region (primers yusX1F and yusX3R).

Example 4

Amylase Yield from *B. subtilis* yusX-deletion Mutants

The yusX-deletion mutant AN151 was transformed with plasmid pKTH10 which constitutively expresses the alpha-amylase AmyQ of *Bacillus amyloliquefaciens*. The resulting strain was named AN155. The yields of amylase from AN155 were determined in duplicate from two independent isolates and compared to yield of amylase from the control strain AN83. Results are shown in table 2; the AN155 strain which carries a yusX deletion, has an increased alpha-amylase yield, which on average is 239% higher than the control strain, AN83, which carries the wild-type copy of the yusX gene.

TABLE 2

Yields of amylase from the AN137 strains (yusX-deletion mutants), and the control strain AN83.

| Strain | Amylase activity (relative) | Average yields | Average yields |
|---|---|---|---|
| AN155-1.1 | 29.9 | 29.8 | 238% |
| AN155-1.2 | 32.2 | | |
| AN155-1.3 | 30.2 | | |
| AN155-2.1 | 28.1 | | |
| AN155-2.2 | 28.9 | | |
| AN155-2.3 | 29.5 | | |
| AN83-1.1 | 12.4 | 12.5 | 100% |
| AN83-1.2 | 12.9 | | |
| AN83-1.3 | 11.5 | | |
| AN83-2.1 | 12.3 | | |
| AN83-2.2 | 11.9 | | |
| AN83-2.3 | 13.8 | | |

Example 5

Construction of *Bacillus licheniformis* yusZ-deletion Mutants

Deletion of the yusZ gene of *Bacillus licheniformis* may be performed by any of the standard methods available. The genomic sequence of *B. licheniformis* is publicly available; the sequence of the *B. licheniformis* yusZ gene is shown in SEQ ID NO: 24, the encoded polypeptide is shown in SEQ ID NO: 25. For example, a PCR product can be generated by use of the technique of splicing by overlap extension (SOE-PCR) as described above (in Plasmids, pAN28). PCR1, which may contain yusZ upstream sequence, can be generated by use of primers yusZlich1F and yusZlich2R, in a PCR reaction with SJ1707 chromosomal DNA as template. PCR2, which may contain yusZ downstream sequence, can be generated by use of primers yusZlich3F and yusZlich4R, in another PCR reaction with SJ1707 chromosomal DNA as template. The spliced product (991 bp, denoted yusZlichSOE), wherein the yusZ gene is reduced from encoding 280aa to only 25aa, can be generated in the second-stage PCR using PCR1 and PCR2 as templates, and yusZlich1F and yusZlich4R as primers. A plasmid denoted "deletion plasmid" can be constructed by cloning of yusZlichSOE in the BsaHI-SacII sites of the temperature sensitive plasmid pAN212b—resulting in plasmid pAN212b-yusZ (=the deletion plasmid). The entire sequence of plasmid pAN212b-yusZ is shown in SEQ ID NO: 26.

The deletion plasmid can be transformed into competent cells of the *B. subtilis* conjugation donor strain PP289-5 (which contains a chromosomal dal-deletion, and plasmids pBC16 and pLS20), and conjugated to *B. licheniformis* AN10R and ANaprH strains by use of standard methods (as described in WO 02/00907). The yusZ deletion can then be transferred from the deletion plasmid to the chromosome of the target *B. licheniformis* strain by double homologous recombination via PCR1 and PCR2, mediated by integration and excision of the temperature sensitive plasmid (as described in example 2). A yusZ-deleted strain can be identified by PCR with primers yusZlich1F and yusZlich4R and verified by standard sequence analysis.

Example 6

10R Protease Yield from *B. licheniformis* yusZ-deletion Mutants

*Bacillus licheniformis* strain SJ1707 was engineered to express protease 10R from *Nocardiopsis prasina* NRLL 18262 (AN10R) to very high levels. The yusZ gene was deleted from AN10R resulting in AN10R-b. The yield of protease from AN10R-b was determined in duplicate from four independent isolates and compared to the yield of protease from the control strain AN10R. The AN10R-b strains (yusZ-deletion mutants) had an increased protease yield, which on average was 72% higher than the control strain AN10R. Results are shown in table 3.

TABLE 3

Yields of Protease 10R from the AN10R-b strains(yusZ-deletion mutants) and the control strain An10R.

| Strain | Protease activity (relative) | Average yields | Average yields |
|---|---|---|---|
| AN10R-B-1.1 | 72.4 | 57 | 172% |
| AN10R-B-1.2 | 24.4 | | |
| AN10R-B-2.1 | 48.0 | | |
| AN10R-B-2.2 | 43.5 | | |
| AN10R-B-3.1 | 63.6 | | |
| AN10R-B-3.2 | 51.7 | | |
| AN10R-B-4.1 | 87.3 | | |
| AN10R-B-4.2 | 65.0 | | |
| AN10R-1.1 | 53.6 | 33 | 100% |
| AN10R-1.2 | 16.1 | | |
| AN10R-2.1 | 12.4 | | |
| AN10R-2.2 | 28.5 | | |
| AN10R-3.1 | 57.9 | | |
| AN10R-3.2 | 49.1 | | |
| AN10R-4.1 | 23.4 | | |
| AN10R-4.2 | 26.8 | | |

Example 7

AprH Protease Yield from *B. licheniformis* yusZ-deletion Mutants

*Bacillus licheniformis* strain SJ1707 was engineered to express the aprH protease gene from *Bacillus clausii* (ANaprH) in very high levels. The yusZ gene was deleted from ANaprH resulting in strain ANaprH-b. The yield of protease from ANaprH-b was determined from four independent isolates (FIG. 1, No's 1-4) and compared to the yield of protease from four independent isolates of the control strain ANaprH by Poly Acrylamid Gel Electrophoresis (PAGE), where the gel was labelled to visualize the protease.

It is clear from the difference in the thickness of the labelled protease bands on the acrylamid gel shown in FIG. 1, that the yusZ-deleted strain (ANaprH-b) produces more aprH-encoded protease than the corresponding reference strain (ANaprH).

Example 8

Apr Protease Yield from *B. subtilis* yusZ-deletion Mutants

*Bacillus subtilis* strain 168 was engineered to express the apr protease gene from *Bacillus amyloliquefaciens* (AN220) to very high levels. The yusZ gene was deleted from AN220 resulting in AN225. The yield of protease from AN225 was determined in duplicate from four independent isolates and compared to the yield of protease from the control strain AN220. The AN225 strains (yusZ-deletion mutants) had an increased protease yield, which on average was 14% higher than the control strain AN220. Results are shown in table 4.

TABLE 4

Yields of Protease 10R from AN10R-b (ΔyusZ) and the control strain An10R..

| Strain | Protease activity (relative) | Average yields | Average yields |
|---|---|---|---|
| AN225-B-1.1 | 42.8 | 44.5 | 114% |
| AN225-B-1.2 | 42.8 | | |
| AN225-B-2.1 | 53.2 | | |
| AN225-B-2.2 | 47.5 | | |
| AN225-B-3.1 | 30.9 | | |
| AN225-B-3.2 | 51.8 | | |
| AN225-B-4.1 | 49.4 | | |
| AN225-B-4.2 | 37.3 | | |
| AN220-1.1 | 59 | 38.9 | 100% |
| AN220-1.2 | 51.8 | | |
| AN220-2.1 | 49 | | |
| AN220-2.2 | 33.6 | | |
| AN220-3.1 | 32.6 | | |
| AN220-3.2 | 23.7 | | |
| AN220-4.1 | 27.1 | | |
| AN220-4.2 | 34.6 | | |

The invention claimed is:

1. An isolated mutated *Bacillus* cell, which has a reduced expression-level of polypeptide having at least 90% sequence identity to the polypeptide of SEQ ID NO: 2, SEQ ID NO: 25, or SEQ ID NO:4, and which secretes higher amounts of at least one heterologous polypeptide of interest, when compared with an otherwise isogenic but non-mutated cell.

2. The cell of claim 1, which is a *B.alkalophilus, B. amyloliquefaciens, B. brevis, B. circulans, B.clausii, B.coagulans, B. lautus, B.lentus, B.licheniformis, B.megaterium, B. stearothermophilus, B. subtilis,* or *B. thuringiensis* cell.

3. The cell of claim 1, wherein the polypeptide has at least 97% sequence identity to the polypeptide of SEQ ID NO: 2, SEQ ID NO: 25 or SEQ ID NO:4.

4. The cell of claim 3, wherein the polypeptide has at least 99% sequence identity to the mature polypeptide of SEQ ID NO: 2, SEQ ID NO: 25 or SEQ ID NO: 4.

5. The cell of claim 3, wherein the polypeptide comprises the polypeptide of SEQ ID NO: 2, SEQ ID NO: 25 or SEQ ID NO: 4.

6. The cell of claim 1, wherein the at least one heterologous polypeptide comprises an enzyme.

7. A method for producing a polypeptide of interest, said method comprising the steps of:
a) cultivating a mutated *Bacillus* cell, which has a reduced expression-level of polypeptide having at least 90% sequence identity to the polypeptide of SEQ ID NO: 2, SEQ ID NO: 25 or SEQ ID NO: 4, and which secretes higher amounts of the polypeptide of interest, when compared with an otherwise isogenic but non-mutated cell; and
b) isolating the polypeptide of interest.

8. The method of claim 7, wherein the cell is a *B.alkalophilus, B. amyloliquefaciens, B. brevis, B.circulans, B.clausii, B.coagulans, B.lautus, B.lentus, B.licheniformis, B.megaterium, B. stearothermophilus, B. subtilis,* or *B. thuringiensis* cell.

9. The method of claim 7, where the cell in step (a) is mutated in a position within SEQ ID NO: 2, SEQ ID NO: 25 and SEQ ID NO: 4.

10. The method of claim 7, wherein the polypeptide has at least 97% sequence identity to the polypeptide of SEQ ID NO: 2, SEQ ID NO: 25 or SEQ ID NO: 4.

11. The method of claim 7, wherein the polypeptide has at least 99% sequence identity to the polypeptide of SEQ ID NO:2, SEQ ID NO: 25 or SEQ ID NO:4.

12. The method of claim 7, wherein the at least one polypeptide of interest comprises an enzyme.

13. An isolated mutated *Bacillus* cell, which has a mutation in a gene encoding a polypeptide having at least 95% sequence identity to the polypeptide of SEQ ID NO: 2, SEQ ID NO: 25, or SEQ ID NO:4, wherein said mutation results in reduced expression of said polypeptide where said *Bacillus* cell secretes a higher amount of at least one heterologous polypeptide of interest compared to an otherwise isogenic but non-mutated *Bacillus* cell.

14. The cell of claim 13, in which the gene is partially of fully deleted from the chromosome.

15. The cell of claim 13, in which the gene comprises at least one frame shift or non-sense mutation.

16. The cell of claim 13, wherein the mutation is in a gene encoding a polypeptide having at least 99% sequence identity to the polypeptide of SEQ ID NO: 2, SEQ ID NO: 25 or SEQ ID NO: 4.

17. The cell of claim 13, wherein the mutation is in a gene encoding a polypeptide consisting of SEQ ID NO: 2.

18. The cell of claim 13, wherein the mutation is in a gene encoding a polypeptide consisting of SEQ ID NO: 25.

19. The cell of claim 13, wherein the mutation is in a gene encoding a polypeptide consisting of SEQ ID NO: 4.

20. The cell of claim 3, wherein the polypeptide consists of the polypeptide of SEQ ID NO: 2.

21. The cell of claim 3, wherein the polypeptide consists of the polypeptide of SEQ ID NO: 25.

22. The cell of claim 3, wherein the polypeptide consists of the polypeptide of SEQ ID NO: 4.

* * * * *

SEQUENCE LISTING

<160> NUMBER OF SEQ ID NOS: 26

<210> SEQ ID NO 1
<211> LENGTH: 843
<212> TYPE: DNA
<213> ORGANISM: Bacillus subtilis 168

<400> SEQUENCE: 1

```
atgaataaaa aaatagccat cgtgacagga gcgtccagcg gcttcggtct gctggcagct      60
gtaaagcttg cccgatcatt tttcgtgata gccacatcaa gacagcctga aaaagcggaa     120
cagcttcgag aattggctgc agcacacaat gtgtctgatt ctattcacat tacagctctc     180
gatgtcaccg atgaacaatc tatagtctca ttcggaaaag ctgttagtgc ttacgcccg      240 atcgatttac tcgttaacaa cgccggaacg gcttatggag gatttatcga ggatgtgccg     300
atggaacatt tcagacaaca atttgaaacg aatgtcttcg gtgtgatcca tgtgacaaaa     360
accgtgctgc cttacataag aaagcatggc ggcgcaaaga ttataaacgt gagcagcatc     420
```

```
agcggactga caggattccc agcgctgtcg ccatatgttt cttccaagca tgcattggaa    480
ggtttttctg aaagcctgcg tatcgagctg cttccgttcg gtatcgaaac cgctttgatc    540
gagccgggct catacaagac atcgatctgg tcaacgtcat tatcaaattt tatgtcggtg    600
cctgctgacg attcagccta tcatcaatac tataaaaaga tcctttccta tgttcaaaaa    660
aacggagaag aaagcggaga tccccaagag gttgccgacc tcatttatca attggcaaca    720
aaacagcaca taagaatttt gcgatacccg atcggaaagg gcatcaagct caccctgctg    780
ttccgatcgc ttttccttg gtctgcgtgg gagtctatcc tgaagaaaaa gctattcagc    840
tga                                                                  843
```

```
<210> SEQ ID NO 2
<211> LENGTH: 280
<212> TYPE: PRT
<213> ORGANISM: Bacillus subtilis 168

<400> SEQUENCE: 2

Met Asn Lys Lys Ile Ala Ile Val Thr Gly Ala Ser Ser Gly Phe Gly
1               5                   10                  15

Leu Leu Ala Ala Val Lys Leu Ala Arg Ser Phe Phe Val Ile Ala Thr
            20                  25                  30

Ser Arg Gln Pro Glu Lys Ala Glu Gln Leu Arg Glu Leu Ala Ala Ala
        35                  40                  45

His Asn Val Ser Asp Ser Ile His Ile Thr Ala Leu Asp Val Thr Asp
    50                  55                  60

Glu Gln Ser Ile Val Ser Phe Gly Lys Ala Val Ser Ala Tyr Ala Pro
65                  70                  75                  80

Ile Asp Leu Leu Val Asn Asn Ala Gly Thr Ala Tyr Gly Gly Phe Ile
                85                  90                  95

Glu Asp Val Pro Met Glu His Phe Arg Gln Gln Phe Glu Thr Asn Val
            100                 105                 110

Phe Gly Val Ile His Val Thr Lys Thr Val Leu Pro Tyr Ile Arg Lys
        115                 120                 125

His Gly Gly Ala Lys Ile Ile Asn Val Ser Ser Ile Ser Gly Leu Thr
    130                 135                 140

Gly Phe Pro Ala Leu Ser Pro Tyr Val Ser Ser Lys His Ala Leu Glu
145                 150                 155                 160

Gly Phe Ser Glu Ser Leu Arg Ile Glu Leu Leu Pro Phe Gly Ile Glu
                165                 170                 175

Thr Ala Leu Ile Glu Pro Gly Ser Tyr Lys Thr Ser Ile Trp Ser Thr
            180                 185                 190

Ser Leu Ser Asn Phe Met Ser Val Pro Ala Asp Ser Ala Tyr His
        195                 200                 205

Gln Tyr Tyr Lys Lys Ile Leu Ser Tyr Val Gln Lys Asn Gly Glu Glu
    210                 215                 220

Ser Gly Asp Pro Gln Glu Val Ala Asp Leu Ile Tyr Gln Leu Ala Thr
225                 230                 235                 240

Lys Gln His Ile Lys Asn Leu Arg Tyr Pro Ile Gly Lys Gly Ile Lys
                245                 250                 255

Leu Thr Leu Leu Phe Arg Ser Leu Phe Pro Trp Ser Ala Trp Glu Ser
            260                 265                 270

Ile Leu Lys Lys Lys Leu Phe Ser
        275                 280
```

<210> SEQ ID NO 3
<211> LENGTH: 1503
<212> TYPE: DNA
<213> ORGANISM: Bacillus subtilis 168

<400> SEQUENCE: 3

```
atgaatcggc tttccgcaga ttttcaatcg tcgctcgtta cattagatca taaacttgtg      60
gacattaatc aagacgtgtg gaatgaattg ttaacaaaac cgggattgcg cgatgtttct     120
tacatattaa atgaaagaag acagagggtt gccgaaaagc ttagccccgg taaggaaaaa     180
ctgatcggaa accttgcggt ggacggatat cacgcttgga gtgacttata caatatggtt     240
gtcgggaaaa tgacgatccc gtatgaggaa acggtgaaa caagcaatt gtctgtcggt      300 caggcggaga atatgatgga tcatcaagac cgtactgtca gaaaaacagt atatgaacgt     360
ttccgccaag cttgggagag caagcaagat attttcagca gcacgctgaa tcatttggcg     420
ggattccggc ttgaaaccta aaagcgcgc ggctgggaga atgtcctgaa ggaaccgctg      480
caaattaaca ggatgaaaaa agaaacactt gatacgatgt ggcaggtcat cactgaaaac     540
aagaagccgt tcgttcagtt tttgaaccgg aaagcatcca tgctcggcct tgaaaaactc     600
agctggtacg atgtcgaggc accgatcggt tctgacggaa aggtctattc gtatgatgaa     660
gccgcaaata tcattaccag ccagtttttca acgtttggca aaaagctgtc ctcattcact    720
gaaaaagcgt tcgggacgg ctggattgag gcggaagaca ggagcggaaa agagtcggc      780 ggcttttgca ccagttttcc ggacagcggg gaatcccgga ttttcatgac attttcggga     840
agcgcctcaa atgtctctac ccttgcgcat gaactcgggc acgcgttcca tcaggaagca     900
atgctcaacg tcaggccgtt aaaccgttcc tacgccatga acgttgcaga acagcttca     960 acgtttgcag atgatgatagt ggcggacgcg actgtccagc aggccgagac gagggaagaa    1020
aagcttgttc ttctggagga taaagtgcaa agaagcgttg cgttcttcat gaacattcac    1080
gcaagatttc tatttgaaac gagattctac gaggaacgaa agcggggagt ggtaccggcc    1140
agccgcttga atgagctgat ggaagaggcg caaagagagg catactgcaa tgcgttagaa    1200
gaatatcatc cgcttttttg ggcatcaaag cttcattttc acatcacgag ggtgccgttt    1260
tacaatttcc cttatacatt cggctacctg ttttctcttg gtatttacgc gttggcgctt    1320
gaagaaaaag acacattcga agagaagtat atggcgctat gcgcgatac ggcttctatg     1380 acagtggagg atttggcgat gaagcatttg ggcgctgaca tcacaaagcg cgatttctgg    1440
gagaatgcca tcaagctggc tgtgcgtgac gccgaaacct ttttacaaat gaccgaatct    1500
taa                                                                  1503
```

<210> SEQ ID NO 4
<211> LENGTH: 500
<212> TYPE: PRT
<213> ORGANISM: Bacillus subtilis 168

<400> SEQUENCE: 4

```
Met Asn Arg Leu Ser Ala Asp Phe Gln Ser Ser Leu Val Thr Leu Asp
1               5                   10                  15

His Lys Leu Val Asp Ile Asn Gln Asp Val Trp Asn Glu Leu Leu Thr
            20                  25                  30

Lys Pro Gly Leu Arg Asp Val Ser Tyr Ile Leu Asn Glu Arg Arg Gln
        35                  40                  45

Arg Val Ala Glu Lys Leu Ser Pro Gly Lys Glu Lys Leu Ile Gly Asn
    50                  55                  60

Leu Ala Val Asp Gly Tyr His Ala Trp Ser Asp Leu Tyr Asn Met Val
```

```
                65                  70                  75                  80
Val Gly Lys Met Thr Ile Pro Tyr Glu Asn Gly Glu Asn Lys Gln
                85                  90                  95
Leu Ser Val Gly Gln Ala Glu Asn Met Met Asp His Gln Asp Arg Thr
                100                 105                 110
Val Arg Lys Thr Val Tyr Glu Arg Phe Arg Gln Ala Trp Glu Ser Lys
                115                 120                 125
Gln Asp Ile Phe Ser Ser Thr Leu Asn His Leu Ala Gly Phe Arg Leu
                130                 135                 140
Glu Thr Tyr Lys Ala Arg Gly Trp Glu Asn Val Leu Lys Glu Pro Leu
145                 150                 155                 160
Gln Ile Asn Arg Met Lys Lys Glu Thr Leu Asp Thr Met Trp Gln Val
                165                 170                 175
Ile Thr Glu Asn Lys Lys Pro Phe Val Gln Phe Leu Asn Arg Lys Ala
                180                 185                 190
Ser Met Leu Gly Leu Glu Lys Leu Ser Trp Tyr Asp Val Glu Ala Pro
                195                 200                 205
Ile Gly Ser Asp Gly Lys Val Tyr Ser Tyr Asp Glu Ala Ala Asn Ile
                210                 215                 220
Ile Thr Ser Gln Phe Ser Thr Phe Gly Lys Lys Leu Ser Ser Phe Thr
225                 230                 235                 240
Glu Lys Ala Phe Arg Asp Gly Trp Ile Glu Ala Glu Asp Arg Ser Gly
                245                 250                 255
Lys Arg Val Gly Gly Phe Cys Thr Ser Phe Pro Asp Ser Gly Glu Ser
                260                 265                 270
Arg Ile Phe Met Thr Phe Ser Gly Ser Ala Ser Asn Val Ser Thr Leu
                275                 280                 285
Ala His Glu Leu Gly His Ala Phe His Gln Glu Ala Met Leu Asn Val
                290                 295                 300
Arg Pro Leu Asn Arg Ser Tyr Ala Met Asn Val Ala Glu Thr Ala Ser
305                 310                 315                 320
Thr Phe Ala Glu Met Ile Val Ala Asp Ala Thr Val Gln Gln Ala Glu
                325                 330                 335
Thr Arg Glu Glu Lys Leu Val Leu Leu Glu Asp Lys Val Gln Arg Ser
                340                 345                 350
Val Ala Phe Phe Met Asn Ile His Ala Arg Phe Leu Phe Glu Thr Arg
                355                 360                 365
Phe Tyr Glu Glu Arg Lys Arg Gly Val Val Pro Ala Ser Arg Leu Asn
                370                 375                 380
Glu Leu Met Glu Glu Ala Gln Arg Glu Ala Tyr Cys Asn Ala Leu Glu
385                 390                 395                 400
Glu Tyr His Pro Leu Phe Trp Ala Ser Lys Leu His Phe His Ile Thr
                405                 410                 415
Arg Val Pro Phe Tyr Asn Phe Pro Tyr Thr Phe Gly Tyr Leu Phe Ser
                420                 425                 430
Leu Gly Ile Tyr Ala Leu Ala Leu Glu Glu Lys Asp Thr Phe Glu Glu
                435                 440                 445
Lys Tyr Met Ala Leu Leu Arg Asp Thr Ala Ser Met Thr Val Glu Asp
                450                 455                 460
Leu Ala Met Lys His Leu Gly Ala Asp Ile Thr Lys Arg Asp Phe Trp
465                 470                 475                 480
Glu Asn Ala Ile Lys Leu Ala Val Arg Asp Ala Glu Thr Phe Leu Gln
                485                 490                 495
```

Met Thr Glu Ser
            500

<210> SEQ ID NO 5
<211> LENGTH: 297
<212> TYPE: DNA
<213> ORGANISM: Bacillus subtilis 168

<400> SEQUENCE: 5
atggcgctgc aaggggtagg ccaaagatgg gatcttgatt cattttttaa gggcgggagc      60
caatcggaag aattcaaagg ttatattgag aagctgtcac aaagtctgcg tgcatttcaa     120
gacaggactg atgcgtttca ggtgcctgaa tcgcctgaag aggctgaagg gctgaccgcg     180
ttgcttgatt taatcgaaca gacatccgtc aagcttcagc aggccggcgc ttttgttgct     240
tgcctccagg cccagaatat caatgatcaa aaggctatag agcatcaggc ctcatga        297

<210> SEQ ID NO 6
<211> LENGTH: 98
<212> TYPE: PRT
<213> ORGANISM: Bacillus subtilis 168

<400> SEQUENCE: 6

Met Ala Leu Gln Gly Val Gly Gln Arg Trp Asp Leu Asp Ser Phe Phe
1               5                   10                  15

Lys Gly Gly Ser Gln Ser Glu Glu Phe Lys Gly Tyr Ile Glu Lys Leu
            20                  25                  30

Ser Gln Ser Leu Arg Ala Phe Gln Asp Arg Thr Asp Ala Phe Gln Val
        35                  40                  45

Pro Glu Ser Pro Glu Glu Ala Glu Gly Leu Thr Ala Leu Leu Asp Leu
    50                  55                  60

Ile Glu Gln Thr Ser Val Lys Leu Gln Gln Ala Gly Ala Phe Val Ala
65                  70                  75                  80

Cys Leu Gln Ala Gln Asn Ile Asn Asp Gln Lys Ala Ile Glu His Gln
                85                  90                  95

Ala Ser

<210> SEQ ID NO 7
<211> LENGTH: 25
<212> TYPE: DNA
<213> ORGANISM: artificial sequence
<220> FEATURE:
<223> OTHER INFORMATION: Primer yusZ1F

<400> SEQUENCE: 7
ccttcccggg gctaagcttt tcggc                                            25

<210> SEQ ID NO 8
<211> LENGTH: 30
<212> TYPE: DNA
<213> ORGANISM: artificial sequence
<220> FEATURE:
<223> OTHER INFORMATION: Primer yusZ2R

<400> SEQUENCE: 8
gatagactcc cacgcgctgg acgctcctgt                                       30

<210> SEQ ID NO 9
<211> LENGTH: 30
<212> TYPE: DNA
<213> ORGANISM: artificial sequence
<220> FEATURE:
<223> OTHER INFORMATION: Primer yusZ2F

```
<400> SEQUENCE: 9
acaggagcgt ccagcgcgtg ggagtctatc                                         30

<210> SEQ ID NO 10
<211> LENGTH: 25
<212> TYPE: DNA
<213> ORGANISM: artificial sequence
<220> FEATURE:
<223> OTHER INFORMATION: Primer yusZ3R

<400> SEQUENCE: 10
aacggtaccc tgaccaagca gacag                                              25

<210> SEQ ID NO 11
<211> LENGTH: 25
<212> TYPE: DNA
<213> ORGANISM: artificial sequence
<220> FEATURE:
<223> OTHER INFORMATION: Primer yusX1F

<400> SEQUENCE: 11
aatgcccggg caagctttac agctg                                              25

<210> SEQ ID NO 12
<211> LENGTH: 30
<212> TYPE: DNA
<213> ORGANISM: artificial sequence
<220> FEATURE:
<223> OTHER INFORMATION: Primer yusX2R

<400> SEQUENCE: 12
ggcgtcacgc acagcaacga gcgacgattg                                         30

<210> SEQ ID NO 13
<211> LENGTH: 30
<212> TYPE: DNA
<213> ORGANISM: artificial sequence
<220> FEATURE:
<223> OTHER INFORMATION: Primer yusX2F

<400> SEQUENCE: 13
caatcgtcgc tcgttgctgt gcgtgacgcc                                         30

<210> SEQ ID NO 14
<211> LENGTH: 25
<212> TYPE: DNA
<213> ORGANISM: artificial sequence
<220> FEATURE:
<223> OTHER INFORMATION: Primer yusX3R

<400> SEQUENCE: 14
aatcggtacc atcataatga ctgtc                                              25

<210> SEQ ID NO 15
<211> LENGTH: 1315
<212> TYPE: DNA
<213> ORGANISM: artificial sequence
<220> FEATURE:
<223> OTHER INFORMATION: PCR product yuszSOEpcr

<400> SEQUENCE: 15
ccttcccggg gctaagcttt tcggcaaccc tctgtcttct ttcatttaat atgtaagaaa        60
catcgcgcaa tcccggtttt gttaacaatt cattccacac gtcttgatta atgtccacaa       120
gtttatgatc taatgtaacg agcgacgatt gaaaatctgc ggaaagccga ttcatgaggc       180
```

```
ctgatgctct atagccttt  gatcattgat attctgggcc tggaggcaag caacaaaagc    240
gccggcctgc tgaagcttga cggatgtctg ttcgattaaa tcaagcaacg cggtcagccc    300
ttcagcctct tcaggcgatt caggcacctg aaacgcatca gtcctgtctt gaaatgcacg    360
cagactttgt gacagcttct caatataacc tttgaattct tccgattggc tcccgccctt    420
aaaaaatgaa tcaagatccc atctttggcc taccccttgc agcgccatat cacaaaaccc    480
ctttccttct ttcgttctat tatagaacaa ttctgaatta ttgtataaaa atttctatta    540
caggcgtcat ttcgtgttca ggatagtaca atagctgtag cagtttaata ggagggttag    600
gatgaataaa aaaatagcca tcgtgacagg agcgtccagc gcgtgggagt ctatcctgaa    660
gaaaaagcta ttcagctgat ctaaattata attattataa tttagtattg attttttattt   720 agtatatgat ataattaagt caacagatca caaggaggac gttatcttat gaaaactgaa    780
aacgcaaaaa caaatcaaac attagttgag aattcactga acacacaatt atcaaactgg    840
tttcttttat actctaagct ccaccgtttc cattggtatg tgaaagggcc tcatttcttt    900
acattgcacg agaaatttga agaactttat gaccatgcgg ctgaaacagt ggataccatc    960
gctgagcgcc tgctggcgat tggcggacag cctgttgcca cagtgaaaga atacactgag   1020
catgcatcta tcacagacgg cggaaacgaa acatcagcat cagaaatggt acaagcattg   1080
gtaaacgact acaacaaat cagcagcgaa tctaaattcg tgatcggcct ggctgaagaa   1140
aatcaagaca atgcgacagc ggacttgttt gtcggattaa ttgaagaagt tgaaaaacaa   1200
gtgtggatgc tttcctctta tttagggtaa caaaaaagct gaaccttaat cgggttcagc   1260
tttttgtttt ttcttagctt gaactgcttt ctgtctgctt ggtcagggta ccgtt        1315
```

<210> SEQ ID NO 16
<211> LENGTH: 6305
<212> TYPE: DNA
<213> ORGANISM: artificial sequence
<220> FEATURE:
<223> OTHER INFORMATION: Plasmid pAN28

<400> SEQUENCE: 16

```
gctaagcttt tcggcaaccc tctgtcttct ttcatttaat atgtaagaaa catcgcgcaa     60
tcccggtttt gttaacaatt cattccacac gtcttgatta atgtccacaa gtttatgatc    120
taatgtaacg agcgacgatt gaaaatctgc ggaaagccga ttcatgaggc ctgatgctct    180 atagccttt  gatcattgat attctgggcc tggaggcaag caacaaaagc gccggcctgc    240
tgaagcttga cggatgtctg ttcgattaaa tcaagcaacg cggtcagccc ttcagcctct    300
tcaggcgatt caggcacctg aaacgcatca gtcctgtctt gaaatgcacg cagactttgt    360
gacagcttct caatataacc tttgaattct tccgattggc tcccgccctt aaaaaatgaa    420
tcaagatccc atctttggcc taccccttgc agcgccatat cacaaaaccc ctttccttct    480
ttcgttctat tatagaacaa ttctgaatta ttgtataaaa atttctatta caggcgtcat    540
ttcgtgttca ggatagtaca atagctgtag cagtttaata ggagggttag gatgaataaa    600
aaaatagcca tcgtgacagg agcgtccagc gcgtgggagt ctatcctgaa gaaaaagcta    660
ttcagctgat ctaaattata attattataa tttagtattg attttttattt agtatatgat    720 ataattaagt caacagatca caaggaggac gttatcttat gaaaactgaa aacgcaaaaa    780
caaatcaaac attagttgag aattcactga acacacaatt atcaaactgg tttcttttat    840
actctaagct ccaccgtttc cattggtatg tgaaagggcc tcatttcttt acattgcacg    900
agaaatttga agaactttat gaccatgcgg ctgaaacagt ggataccatc gctgagcgcc    960
```

```
tgctggcgat tggcggacag cctgttgcca cagtgaaaga atacactgag catgcatcta    1020
tcacagacgg cggaaacgaa acatcagcat cagaaatggt acaagcattg gtaaacgact    1080
acaaacaaat cagcagcgaa tctaaattcg tgatcggcct ggctgaagaa atcaagaca     1140 atgcgacagc ggacttgttt gtcggattaa ttgaagaagt tgaaaaacaa gtgtggatgc    1200
tttcctctta tttagggtaa caaaaaagct gaaccttaat cgggttcagc ttttttgtttt   1260 ttcttagctt gaactgcttt ctgtctgctt ggtcagggta ccattttgac ggaaccgatt    1320
gggacgagtc ccgaaagctg aaccgcatct ataagtttca aggaaaggct tgggattggg    1380
aagtttccaa tgaaaacggc aactatgatt atttgatgta tgccgacatc gattatgacc    1440
atcctgatgt cgcagcagaa attaagagat ggggcacttg gtatgccaat gaactgcaat    1500
tggacggaaa ccgtcttgat gctgtcaaac acattaaatt ttcttttttg cgggattggg    1560
ttaatcatgt cagggaaaaa acggggaagg aaatgtttac ggtagctgaa tattggcaga    1620
atgacttggg cgcgctggaa aactatttga acaaacaaa ttttaatcat tcagtgtttg     1680
acgtgccgct tcattatcag ttccatgctg catcgacaca gggaggcggc tatgatatga    1740
ggaaattgct gaagggtacg gtcgtttcca agcatccgtt gaaatcggtt acatttgtcg    1800
ataaccatga tacacagccg gggcaatcgc ttgagtcgac tgtccaaaca tggtttaagc    1860
cgcttgctta cgcttttatt ctcacaaggg aatctggata ccctcaggtt ttctacgggg    1920
atatgtacgg gacgaaagga gactcccagc gcgaaattcc tgccttgaaa cacaaaattg    1980
aaccgatctt aaaagcgaga aaacagtatg cgtacgagc acagcatgat tatttcgacc     2040
accatgacat tgtcggctgg acaagggaag gcgacagctc ggttgcaaat tcaggtttgg    2100
cggcattaat aacagacgga cccgtgtggg caaagcgaat gtatgtcggc cggcaaaacg    2160
ccggtgagac atggcatgac attaccggaa accgttcgga gccggttgtc atcaattcgg    2220
aaggctgggg agagtttcac gtaaacgcg ggtcggtttc aatttatgtt caaagataga     2280
agagcagaga ggacggattt cctgaaggaa atccgttttt ttattttgcc cgtcttataa    2340
atttcgttga ttcattttta taattaattt taacaaagtg tcataagccc tcaggaatat    2400
tgctgacagt ttagaatccc taggtaaggc ggggatgaaa tggcaacgtt atctgatgta    2460
gcaaagaaag aaatgtgtcg aaaatgacgg tatcgcgggt gatcaatcat cctgagactg    2520
tgacggatga attgaaaaag cttgcatgcc tgcaggtcga ttcacaaaaa ataggcacac    2580
gaaaaacaag ttaagggatg cagtttatgc atcccttaac ttacttatta ataatttat    2640 agctattgaa aagagataag aattgttcaa agctaatatt gtttaaatcg tcaattcctg    2700
catgttttaa ggaattgtta aattgatttt ttgtaaatat ttcttgtat tctttgttaa     2760 cccatttcat aacgaaataa ttatactttt gtttatcttt gtgtgatatt cttgattttt    2820
ttctacttaa tctgataagt gagctattca ctttaggttt aggatgaaaa tattctcttg    2880
gaaccatact taatatagaa atatcaactt ctgccattaa aagtaatgcc aatgagcgtt    2940
ttgtatttaa taatcttta gcaaacccgt attccacgat taaataaatc tcattagcta     3000
tactatcaaa acaattttg cgtattatat ccgtacttat gttataaggt atattaccat     3060
atattttata ggattggttt ttaggaaatt taaactgcaa tatatccttg tttaaaactt    3120
ggaaattatc gtgatcaaca gtttattttt ctgtagtttt gcataattta tggtctattt    3180
caatggcagt tacgaaatta caactcttta ctaattcaag ggtaaaatgg ccttttcctg    3240
agccgatttc aaagatatta tcatgttcat ttaatccttat atttgtcatt atttttatcta  3300 tattatgttt tgaagtaata aagttttgac tgtgttttat attttctcg ttcattataa     3360
```

```
ccctctttaa tttggttata tgaattttgc ttattaacga ttcattataa ccacttattt    3420
tttgtttggt tgataatgaa ctgtgctgat tacaaaaata ctaaaaatgc ccatatttt     3480
tcctccttat aaaattagta taattatagc acgagctctg ataaatatga acatgatgag    3540
tgatcgttaa atttatactg caatcggatg cgattattga ataaagata tgagagattt     3600
atctaatttc ttttttcttg taaaaaaaga aagttcttaa aggttttata gttttggtcg    3660
tagagcacac ggtttaacga cttaattacg aagtaaataa gtctagtgtg ttagacttta    3720
tgaaatctat atacgtttat atatatttat tatccggagg tgtagcatgt ctcattcaat    3780
tttgagggtt gccagagtta aaggatcaag taatacaaac gggatacaaa gacataatca    3840
aagagagaat aaaaactata ataataaga cataaatcat gaggaaacat ataaaaatta     3900
tgatttgatt aacgcacaaa atataaagta taaagataaa attgatgaaa cgattgatga    3960
gaattattca gggaaacgta aaattcggtc agatgcaatt cgacatgtgg acggactggt    4020
tacaagtgat aaagatttct ttgatgattt aagcggagaa gaaatagaac gattttttaa    4080
agatagcttg gagtttctag aaaatgaata cggtaaggaa aatatgctgt atgcgactgt    4140
ccatctggat gaaagagtcc cacatatgca ctttggtttt gtccctttaa cagaggacgg    4200
gagattgtct gcaaaagaac agttaggcaa caagaaagac tttactcaat tacaagatag    4260
atttaatgag tatgtgaatg agaaaggtta tgaacttgaa agaggcacgt ccaaagaggt    4320
tacagaacga gaacataaag cgatggatca gtacaagaaa gatactgtat ttcataaaca    4380
ggaactgcaa gaagttaagg atgagttaca gaaggcaaat aagcagttac agagtggaat    4440
agagcatatg aggtctacga aacccttga ttatgaaaat gagcgtacag gtttgttctc    4500
tggacgtgaa gagactggta gaaagatatt aactgctgat gaatttgaac gcctgcaaga    4560
aacaatctct tctgcagaac ggattgttga tgattacgaa atattaaga gcacagacta     4620
ttacacagaa aatcaagaat taaaaaaacg tagagagagt ttgaaagaag tagtgaatac    4680
atggaaagag gggtatcacg aaaaaagtaa agaggttaat aaattaaagc gagagaatga    4740
tagtttgaat gagcagttga atgtatcaga gaaatttcaa gctagtacag tgactttata    4800
tcgtgctgcg agggcgaatt tccctgggtt tgagaaaggg tttaataggc ttaaagagaa    4860
attctttaat gattccaaat ttgagcgtgt gggacagttt atggatgttg tacaggataa    4920
tgtccagaag gtcgatagaa agcgtgagaa acagcgtaca gacgatttag agatgtagag    4980
gtactttat gccgagaaaa ctttttgcgt gtgacagtcc ttaaaatata cttagagcgt     5040
aagcgaaagt agtagcgaca gctattaact ttcggtttca aagctctagg atttttaatg    5100
gacgcagcgc atcacacgca aaaggaaat tggaataaat gcgaaatttg agatgttaat     5160
taaagacctt tttgaggtct ttttttctta gattttggg gttatttagg ggagaaaaca    5220
taggggta ctacgacctc cccctaggt gtccattgtc cattgtccaa acaaataaat        5280
aaatattggg ttttaatgt taaaggttg ttttttatgt taaagtgaaa aaaacagatg      5340
ttgggaggta cagtgatggt tgtagataga aagaagaga aaaagttgc tgttactta        5400
agacttacaa cagaagaaaa tgagatatta aatagaatca agaaaaata taatattagc     5460
aaatcagatg caaccggtat tctaataaaa aaatatgcaa aggaggaata cggtgcattt    5520
taaacaaaaa aagatagaca gcactggcat gctgcctatc tatgactaaa ttttgttaag    5580
tgtattagca ccgttattat atcatgagcg aaaatgtaat aaaagaaact gaaaacaaga    5640
aaaattcaag aggacgtaat tggacatttg ttttatatcc agaatcagca aaagccgagt    5700
ggttagagta tttaaaagag ttacacattc aatttgtagt gtctccatta catgataggg    5760
```

| | |
|---|---|
| atactgatac agaaggtagg atgaaaaaag agcattatca tattctagtg atgtatgagg | 5820 |
| gtaataaatc ttatgaacag ataaaaataa ttacagaaga attgaatgcg actattccgc | 5880 |
| agattgcagg aagtgtgaaa ggtcttgtga gatatatgct tcacatggac gatcctaata | 5940 |
| aatttaaata tcaaaagaa gatatgatag tttatggcgg tgtagatgtt gatgaattat | 6000 |
| taaagaaaac aacaacagat agatataaat taattaaaga aatgattgag tttattgatg | 6060 |
| aacaaggaat cgtagaattt aagagtttaa tggattatgc aatgaagttt aaatttgatg | 6120 |
| attggttccc gcttttatgt gataactcgg cgtatgttat tcaagaatat ataaaatcaa | 6180 |
| atcggtataa atctgaccga tagattttga atttaggtgt cacaagacac tcttttttcg | 6240 |
| caccagcgaa aactggttta agccgactgc gcaaaagaca taatcgactc tagaggatcc | 6300 |
| ccggg | 6305 |

<210> SEQ ID NO 17
<211> LENGTH: 1090
<212> TYPE: DNA
<213> ORGANISM: artificial sequence
<220> FEATURE:
<223> OTHER INFORMATION: PCR product yusxSOEpcr

<400> SEQUENCE: 17

| | |
|---|---|
| aatgcccggg caagcttac agctgccagc agaccgaagc cgctggacgc tcctgtcacg | 60 |
| atggctattt ttttattcat cctaaccctc ctattaaact gctacagcta ttgtactatc | 120 |
| ctgaacacga aatgacgcct gtaatagaaa ttttttataca ataattcaga attgttctat | 180 |
| aatagaacga agaaggaaa ggggttttgt gatatggcgc tgcaagggt aggccaaaga | 240 |
| tgggatcttg attcattttt taagggcggg agccaatcgg aagaattcaa aggttatatt | 300 |
| gagaagctgt cacaaagtct gcgtgcattt caagacagga ctgatgcgtt tcaggtgcct | 360 |
| gaatcgcctg aagaggctga agggctgacc gcgttgcttg atttaatcga acagacatcc | 420 |
| gtcaagcttc agcaggccgg cgcttttgtt gcttgcctcc aggcccagaa tatcaatgat | 480 |
| caaaaggcta tagagcatca ggcctcatga atcggctttc gcagatttt caatcgtcgc | 540 |
| tcgttgctgt gcgtgacgcc gaaacctttt tacaaatgac cgaatcttaa agaaaaagcc | 600 |
| gtggcgttaa atgccccggc ttttcaatt cttctctgaa tgaggattc attctctgga | 660 |
| tatacctaaa ataaatggaa tcctacaggg gggaaacata tgcatttgat cagagcagcc | 720 |
| ggggctgtat gtctcgcagt ggttctgatt gcgggctgcc gtttcaatga agaccagcat | 780 |
| caggcagaag gagaaaatac agccgtcacc cagctgaagt ccgttcccta cagtaatttt | 840 |
| tcgcttcgtg tgagctacgg ggatggtgag cataaccgtt atgaaggaat ctatacaaag | 900 |
| aacgggactc aggaaaaagc ggaaatacag gataagctct ccggtgtcaa tcaggaagga | 960 |
| gaagaagcgt tagatgagat gaaaatgatt ttgagcgagc tttccgtgac agaccaaatg | 1020 |
| gctgaaacag aagtgataca cagtgtgctg cagcatttta atctggacag tcattatgat | 1080 |
| ggtaccgatt | 1090 |

<210> SEQ ID NO 18
<211> LENGTH: 6079
<212> TYPE: DNA
<213> ORGANISM: artificial sequence
<220> FEATURE:
<223> OTHER INFORMATION: Plasmid pAN23

<400> SEQUENCE: 18

| | |
|---|---|
| caagctttac agctgccagc agaccgaagc cgctggacgc tcctgtcacg atggctattt | 60 |

| | |
|---|---|
| ttttattcat cctaaccctc ctattaaact gctacagcta ttgtactatc ctgaacacga | 120 |
| aatgacgcct gtaatagaaa tttttataca ataattcaga attgttctat aatagaacga | 180 |
| aagaaggaaa ggggttttgt gatatggcgc tgcaagtggt aggccaaaga tgggatcttg | 240 |
| attcatttt taagggcggg agccaatcgg aagaattcaa aggttatatt gagaagctgt | 300 |
| cacaaagtct gcgtgcattt caagacagga ctgatgcgtt tcaggtgcct gaatcgcctg | 360 |
| aagaggctga agggctgacc gcgttgcttg atttaatcga acagacatcc gtcaagcttc | 420 |
| agcaggccgg cgcttttgtt gcttgcctcc aggcccagaa tatcaatgat caaaaggcta | 480 |
| tagagcatca ggcctcatga atcggctttc cgcagatttt caatcgtcgc tcgttgctgt | 540 |
| gcgtgacgcc gaaacctttt tacaaatgac cgaatcttaa agaaaaagcc gtggcgttaa | 600 |
| atgccccggc tttttcaatt cttctctgaa tgaggatttc attctctgga tatacctaaa | 660 |
| ataaatggaa tcctacaggg gggaaacata tgcatttgat cagagcagcc ggggctgtat | 720 |
| gtctcgcagt ggttctgatt gcgggctgcc gtttcaatga agaccagcat caggcagaag | 780 |
| gagaaaatac agccgtcacc cagctgaagt ccgttcccta cagtaatttt tcgcttcgtg | 840 |
| tgagctacgg ggatggtgag cataaccgtt atgaaggaat ctatacaaag aacgggactc | 900 |
| aggaaaaagc ggaaatacag gataagctct ccggtgtcaa tcaggaagga gaagaagcgt | 960 |
| tagatgagat gaaaatgatt ttgagcgagc tttccgtgac agaccaaatg gctgaaacag | 1020 |
| aagtgataca cagtgtgctg gcagcattta atctggacag tcattatgat ggtaccattt | 1080 |
| tgacggaacc gattgggacg agtcccgaaa gctgaaccgc atctataagt ttcaaggaaa | 1140 |
| ggcttgggat tgggaagttt ccaatgaaaa cggcaactat gattatttga tgtatgccga | 1200 |
| catcgattat gaccatcctg atgtcgcagc agaaattaag agatgggca cttggtatgc | 1260 |
| caatgaactg caattggacg gaaaccgtct tgatgctgtc aaacacatta aatttttcttt | 1320 |
| tttgcgggat tgggttaatc atgtcaggga aaaacggg aaggaaatgt tacggtagc | 1380 |
| tgaatattgg cagaatgact tgggcgcgct ggaaaactat ttgaacaaaa caaatttaa | 1440 |
| tcattcagtg ttttgacgtgc cgcttcatta tcagttccat gctgcatcga cacagggagg | 1500 |
| cggctatgat atgaggaaat tgctgaaggg tacggtcgtt tccaagcatc cgttgaaatc | 1560 |
| ggttacattt gtcgataacc atgatacaca gccggggcaa tcgcttgagt cgactgtcca | 1620 |
| aacatggttt aagccgcttg cttacgcttt tattctcaca agggaatctg gataccctca | 1680 |
| ggtttctac ggggatatgt acgggacgaa aggagactcc cagcgcgaaa ttcctgcctt | 1740 |
| gaaacacaaa attgaaccga tcttaaaagc gagaaaacag tatgcgtacg gagcacagca | 1800 |
| tgattatttc gaccaccatg acattgtcgg ctggacaagg gaaggcgaca gctcggttgc | 1860 |
| aaaattcaggt ttggcggcat taataacaga cggacccggt ggggcaaagc gaatgtatgt | 1920 |
| cggccggcaa aacgccggtg agacatggca tgacattacc ggaaaccgtt cggagccggt | 1980 |
| tgtcatcaat tcggaaggct ggggagagtt tcacgtaaac ggcgggtcgg tttcaattta | 2040 |
| tgttcaaaga tagaagagca gagaggacgg atttcctgaa ggaaatccgt ttttttattt | 2100 |
| tgcccgtctt ataaatttcg ttgattacat tttataatta atttaacaa agtgtcataa | 2160 |
| gccctcagga atattgctga cagttttagaa tccctaggta aggcggggat gaaatggcaa | 2220 |
| cgttatctga tgtagcaaag aaagaaatgt gtcgaaaatg acggtatcgc gggtgatcaa | 2280 |
| tcatcctgag actgtgacgg atgaattgaa aaagcttgca tgcctgcagg tcgattcaca | 2340 |
| aaaaatagc acacgaaaaa caagttaagg gatgcagttt atgcatccct taacttactt | 2400 |
| attaaataat ttatagctat tgaaaagaga taagaattgt tcaaagctaa tattgtttaa | 2460 |

```
atcgtcaatt cctgcatgtt ttaaggaatt gttaaattga ttttttgtaa atattttctt    2520
gtattctttg ttaacccatt tcataacgaa ataattatac ttttgtttat ctttgtgtga    2580
tattcttgat ttttttctac ttaatctgat aagtgagcta ttcactttag gtttaggatg    2640
aaaatattct cttggaacca tacttaatat agaaatatca acttctgcca ttaaaagtaa    2700
tgccaatgag cgttttgtat ttaataatct tttagcaaac ccgtattcca cgattaaata    2760
aatctcatta gctatactat caaaaacaat tttgcgtatt atatccgtac ttatgttata    2820
aggtatatta ccatatattt tataggattg gtttttagga aatttaaact gcaatatatc    2880
cttgttaaaa acttggaaat tatcgtgatc aacaagttta ttttctgtag ttttgcataa    2940
tttatggtct atttcaatgg cagttacgaa attacacctc tttactaatt caagggtaaa    3000
atggcctttt cctgagccga tttcaaagat attatcatgt tcatttaatc ttatatttgt    3060
cattatttta tctatattat gttttgaagt aataaagttt tgactgtgtt ttatattttt    3120
ctcgttcatt ataaccctct ttaatttggt tatatgaatt ttgcttatta acgattcatt    3180
ataaccactt ttttttgtt tggttgataa tgaactgtgc tgattacaaa aatactaaaa    3240
atgcccatat ttttcctcc ttataaaatt agtataatta tagcacgagc tctgataaat    3300
atgaacatga tgagtgatcg ttaaatttat actgcaatcg gatgcgatta ttgaataaaa    3360
gatatgagag atttatctaa tttctttttt cttgtaaaaa aagaaagttc ttaaaggttt    3420
tatagttttg gtcgtagagc acacggttta acgacttaat tacgaagtaa ataagtctag    3480
tgtgttagac tttatgaaat ctatatacgt ttatatatat ttattatccg gaggtgtagc    3540
atgtctcatt caattttgag ggttgccaga gttaaaggat caagtaatac aaacgggata    3600
caaagacata atcaaagaga gaataaaaac tataataata aagacataaa tcatgaggaa    3660
acatataaaa attatgattt gattaacgca caaaatataa agtataaaga taaaattgat    3720
gaaacgattg atgagaatta ttcagggaaa cgtaaaattc ggtcagatgc aattcgacat    3780
gtggacggac tggttacaag tgataaagat ttctttgatg atttaagcgg agaagaaata    3840
gaacgatttt ttaaagatag cttggagttt ctagaaaatg aatacggtaa ggaaaatatg    3900
ctgtatgcga ctgtccatct ggatgaaaga gtcccacata tgcactttgg ttttgtccct    3960
ttaacagagg acgggagatt gtctgcaaaa gaacagttag gcaacaagaa agactttact    4020
caattacaag atagatttaa tgagtatgtg aatgagaaag gttatgaact tgaaagaggc    4080
acgtccaaag aggttacaga acgagaacat aaagcgatgg atcagtacaa gaaagatact    4140
gtatttcata acaggaact gcaagaagtt aaggatgagt tacagaaggc aaataagcag    4200
ttacagagtg gaatagagca tatgaggtct acgaaacct tgattatga aaatgagcgt    4260 acaggtttgt tctctggacg tgaagagact ggtagaaaga tattaactgc tgatgaattt    4320
gaacgcctgc aagaaacaat ctcttctgca gaacggattg ttgatgatta cgaaaatatt    4380
aagagcacag actattacac agaaaatcaa gaattaaaaa aacgtagaga gagtttgaaa    4440
gaagtagtga atacatggaa agaggggtat cacgaaaaaa gtaaagaggt taataaatta    4500
aagcgagaga atgatagttt gaatgagcag ttgaatgtat cagagaaatt tcaagctagt    4560
acagtgactt tatatcgtgc tgcgagggcg aatttccctg gtttgagaa agggtttaat    4620 aggcttaaag agaaattctt taatgattcc aaatttgagc gtgtgggaca gtttatggat    4680
gttgtacagg ataatgtcca gaaggtcgat agaaagcgtg agaaacagcg tacagacgat    4740
ttagagatgt agaggtactt ttatgccgag aaaactttt gcgtgtgaca gtccttaaaa    4800
tatacttaga gcgtaagcga aagtagtagc gacagctatt aactttcggt ttcaaagctc    4860
```

```
taggattttt aatggacgca gcgcatcaca cgcaaaaagg aaattggaat aaatgcgaaa    4920
tttgagatgt taattaaaga cctttttgag gtctttttt  cttagatttt tggggttatt    4980
taggggagaa acatagggg  ggtactacga cctccccct  aggtgtccat tgtccattgt    5040
ccaaacaaat aaataaatat tgggtttta  atgttaaaag gttgttttt  atgttaaagt    5100 gaaaaaaca  gatgttggga ggtacagtga tggttgtaga tagaaaagaa gagaaaaaag    5160
ttgctgttac tttaagactt acaacagaag aaaatgagat attaaataga atcaaagaaa    5220
aatataatat tagcaaatca gatgcaaccg gtattctaat aaaaaaatat gcaaaggagg    5280
aatacggtgc atttaaaca  aaaaaagata gacagcactg gcatgctgcc tatctatgac    5340 taaatttgt  taagtgtatt agcaccgtta ttatatcatg agcgaaaatg taataaaaga    5400
aactgaaaac aagaaaaatt caagaggacg taattggaca tttgttttat atccagaatc    5460
agcaaaagcc gagtggttag agtatttaaa agagttacac attcaatttg tagtgtctcc    5520
attacatgat agggatactg atacagaagg taggatgaaa aaagagcatt atcatattct    5580
agtgatgtat gagggtaata aatcttatga acagataaaa ataattacag aagaattgaa    5640
tgcgactatt ccgcagattg caggaagtgt gaaaggtctt gtgagatata tgcttcacat    5700
ggacgatcct aataaattta aatatcaaaa agaagatatg atagtttatg gcggtgtaga    5760
tgttgatgaa ttattaaaga aaacaacaac agatagatat aaattaatta agaaaatgat    5820
tgagtttatt gatgaacaag gaatcgtaga atttaagagt ttaatggatt atgcaatgaa    5880
gtttaaattt gatgattggt tcccgctttt atgtgataac tcggcgtatg ttattcaaga    5940
atatataaaa tcaaatcggt ataaatctga ccgatagatt ttgaatttag gtgtcacaag    6000
acactctttt ttcgcaccag cgaaaactgg tttaagccga ctgcgcaaaa gacataatcg    6060
actctagagg atccccggg                                                6079
```

```
<210> SEQ ID NO 19
<211> LENGTH: 35
<212> TYPE: DNA
<213> ORGANISM: artificial sequence
<220> FEATURE:
<223> OTHER INFORMATION: Primer yusZlich1F

<400> SEQUENCE: 19
tcagcagccc gcggagcagc cgttttaatg gaacc                               35

<210> SEQ ID NO 20
<211> LENGTH: 40
<212> TYPE: DNA
<213> ORGANISM: artificial sequence
<220> FEATURE:
<223> OTHER INFORMATION: Primer yusZlich2R

<400> SEQUENCE: 20
atgaccgcac gttcccaaat gctcgtcgcg cccgttacaa                          40

<210> SEQ ID NO 21
<211> LENGTH: 40
<212> TYPE: DNA
<213> ORGANISM: artificial sequence
<220> FEATURE:
<223> OTHER INFORMATION: Primer yusZlich3F

<400> SEQUENCE: 21
ttgtaacggg cgcgacgagc atttgggaac gtgcggtcat                          40
```

```
<210> SEQ ID NO 22
<211> LENGTH: 36
<212> TYPE: DNA
<213> ORGANISM: artificial sequence
<220> FEATURE:
<223> OTHER INFORMATION: Primer yusZlich4R

<400> SEQUENCE: 22
gcggatttga cgtcaatcgc ttaccagtgc ggaaac                               36

<210> SEQ ID NO 23
<211> LENGTH: 4350
<212> TYPE: DNA
<213> ORGANISM: artificial sequence
<220> FEATURE:
<223> OTHER INFORMATION: Plasmid pAN212b

<400> SEQUENCE: 23
aattcagatc cttattgttc ccgcgggacg tcgattcaca aaaataggca cacgaaaaac      60
aagtaaggga tgcagtttat gcatccctta acttacttat taaataattt atagctattg    120
aaaagagata agaattgttc aaagctaata ttgtttaaat cgtcaattcc tgcatgtttt    180
aaggaattgt taaattgatt ttttgtaaat attttcttgt attctttgtt aacccatttc    240
ataacgaaat aattatactt tgtttatctt tgtgtgata ttcttgattt ttttctactt     300
aatctgataa gtgagctatt cactttaggt ttaggtgaa atattctct tggaaccata      360 cttaatatag aaatatcaac ttctgccatt aaaagtaatg ccaatgagcg ttttgtattt    420
aataatcttt tagcaaaccc gtattccacg attaaataaa tctcattagc tatactatca    480
aaacaatttt gcgtattat atccgtactt atgttataag gtatattacc atatatttta    540
taggattggt tttaggaaa tttaaactgc aatatatcct tgtttaaaac ttggaaatta     600
tcgtgatcaa caagtttatt ttctgtagtt ttgcataatt tatggtctat ttcaatggca    660
gttacgaaat tacacctctt tactaattca agggtaaaat ggccttttcc tgagccgatt    720
tcaaagatat tatcatgttc atttaatctt atatttgtca ttatttatc tatattatgt     780 tttgaagtaa taaagttttg actgtgtttt atattttct cgttcattat aaccctcttt     840
aatttggtta tatgaatttt gcttattaac gattcattat aaccacttat tttttgtttg    900
gttgataatg aactgtgctg attacaaaaa tactaaaaat gcccatattt tttcctcctt    960
ataaaattag tataattata gcacgagctc tgataaatat gaacatgatg agtgatcgtt   1020
aaatttatac tgcaatcgga tgcgattatt gaataaaaga tatgagagat ttatctaatt   1080 tctttttttct tgtaaaaaaa gaaagttctt aaaggtttta tagtttggt cgtagagcac    1140 acggtttaac gacttaatta cgaagtaaat aagtctagtg tgttagactt tatgaaatct   1200
atatacgttt atatatattt attatccgga ggtgtagcat gtctcattca attttgaggg   1260
ttgccagagt taaggatca agtaatacaa acgggataca aagacataat caaagagaga   1320
ataaaaacta taataataaa gacataaatc atgaggaaac atataaaaat tatgatttga   1380
ttaacgcaca aaatataaag tataaagata aaattgatga acgattgat gagaattatt    1440 cagggaaacg taaaattcgg tcagatgcaa ttcgacatgt ggacggactg gttacaagtg   1500
ataaagattt ctttgatgat taagcggag aagaaataga acgattttt aaagatagct    1560 tggagtttct agaaaatgaa tacggtaagg aaaatatgct gtatgcgact gtccatctgg   1620
atgaaagagt cccacatatg cactttggtt ttgtcccttt aacagaggac gggagattgt   1680
ctgcaaaaga acagttaggc aacaagaaag actttactca attacaagat agatttaatg   1740
agtatgtgaa tgagaaaggt tatgaacttg aaagaggcac gtccaaagag gttacagaac   1800
```

```
gagaacataa agcgatggat cagtacaaga aagatactgt atttcataaa caggaactgc    1860
aagaagttaa ggatgagtta cagaaggcaa ataagcagtt acagagtgga atagagcata    1920
tgaggtctac gaaacccttt gattatgaaa atgagcgtac aggtttgttc tctggacgtg    1980
aagagactgg tagaaagata ttaactgctg atgaatttga acgcctgcaa gaaacaatct    2040
cttctgcaga acggattgtt gatgattacg aaaatattaa gagcacagac tattacacag    2100
aaaatcaaga attaaaaaaa cgtagagaga gtttgaaaga agtagtgaat acatggaaag    2160
aggggtatca cgaaaaaagt aaagaggtta ataaattaaa gcgagagaat gatagtttga    2220
atgagcagtt gaatgtatca gagaaatttc aagctagtac agtgacttta tatcgtgctg    2280
cgagggcgaa tttccctggg tttgagaaag ggtttaatag gcttaaagag aaattcttta    2340
atgattccaa atttgagcgt gtgggacagt ttatggatgt tgtacaggat aatgtccaga    2400
aggtcgatag aaagcgtgag aaacagcgta cagacgattt agagatgtag aggtactttt    2460
atgccgagaa aacttttgc gtgtgacagt ccttaaaata tacttagagc gtaagcgaaa    2520
gtagtagcga cagctattaa ctttcggttt caaagctcta ggatttttaa tggacgcagc    2580
gcatcacacg caaaaaggaa attggaataa atgcgaaatt tgagatgtta attaaagacc    2640 ttttgaggt cttttttct tagattttg gggttattta ggggagaaaa cataggggg       2700 tactacgacc tcccccctag gtgtccattg tccattgtcc aaacaaataa ataaatattg    2760 ggttttaat gttaaaaggt tgtttttat gttaaagtga aaaaacaga tgttgggagg       2820 tacagtgatg gttgtagata gaaaagaaga gaaaaaagtt gctgttactt taagacttac    2880
aacagaagaa aatgagatat taaatagaat caaagaaaaa tataatatta gcaaatcaga    2940
tgcaaccggt attctaataa aaaaatatgc aaaggaggaa tacggtgcat tttaaacaaa    3000
aaaagataga cagcactggc atgctgccta tctatgacta aattttgtta agtgtattag    3060
caccgttatt atatcatgag cgaaaatgta ataaagaaa  ctgaaaacaa gaaaaattca    3120
agaggacgta attggacatt tgttttatat ccagaatcag caaaagccga gtggttagag    3180
tatttaaaag agttacacat tcaatttgta gtgtctccat tacatgatag ggatactgat    3240
acagaaggta ggatgaaaaa agagcattat catattctag tgatgtatga gggtaataaa    3300
tcttatgaac agataaaaat aattacagaa gaattgaatg cgactattcc gcagattgca    3360
ggaagtgtga aggtcttgt gagatatatg cttcacatgg acgatcctaa taaatttaaa    3420
tatcaaaaag aagatatgat agtttatggc ggtgtagatg ttgatgaatt attaaagaaa    3480
acaacaacag atagatataa attaattaaa gaaatgattg agtttattga tgaacaagga    3540
atcgtagaat ttaagagttt aatggattat gcaatgaagt ttaaatttga tgattggttc    3600
ccgcttttat gtgataactc ggcgtatgtt attcaagaat atataaaatc aaatcggtat    3660
aaatctgacc gatagatttt gaatttaggt gtcacaagac actcttttt cgcaccagcg    3720 aaaactggtt taagccgact gcgcaaaaga cataatcgac tctagaggat ccccgggtac    3780
cgagctctgc cttttagtcc agctgatttc acttttgca ttctacaaac tgcataactc     3840
atatgtaaat cgctcctttt taggtggcac aaatgtgagg catttttcgct ctttccggca   3900 accacttcca gtaaagtat aacacactat actttatatt cataaagtgt gtgctctgcg    3960
aggctgtcgg cagtgccgac caaaaccata aaacctttaa gacctttctt tttttacga    4020 gaaaaagaa acaaaaaaac ctgccctctg ccacctcagc aaagggggt tttgctctcg      4080 tgctcgttta aaaatcagca agggacaggt agtattttt gagaagatca ctcaaaaaat     4140
ctccaccttt aaaccccttgc caattttat tttgtccgtt ttgtctagct taccgaaagc    4200
```

-continued

```
cagactcagc aagaataaaa ttttattgt ctttcggttt tctagtgtaa cggacaaaac    4260
cactcaaaat aaaaaagata caagagaggt ctctcgtatc ttttattcag caatcgcgcc    4320
cgattgctga acagattaat aatgagctcg                                      4350
```

<210> SEQ ID NO 24
<211> LENGTH: 843
<212> TYPE: DNA
<213> ORGANISM: Bacillus licheniformis SJ1707
<220> FEATURE:
<221> NAME/KEY: CDS
<222> LOCATION: (1)..(840)
<223> OTHER INFORMATION: YusZ

<400> SEQUENCE: 24

```
ttg aac aat aaa atc gca att gta acg ggc gcg acg agc gga ttt ggt     48
Leu Asn Asn Lys Ile Ala Ile Val Thr Gly Ala Thr Ser Gly Phe Gly
1               5                   10                  15 tta ttg acc gct tta aaa ctc gca agc act cat ttc gta atc gca acg     96
Leu Leu Thr Ala Leu Lys Leu Ala Ser Thr His Phe Val Ile Ala Thr
            20                  25                  30 gcg cgc cat cca gaa aaa gcg gaa gct ctg cgg aac cgt ata gcg gag    144
Ala Arg His Pro Glu Lys Ala Glu Ala Leu Arg Asn Arg Ile Ala Glu
        35                  40                  45 ctg tcg atc gag tca tcg att gcc gtc gct gaa ctt gat gtc aca aac    192
Leu Ser Ile Glu Ser Ser Ile Ala Val Ala Glu Leu Asp Val Thr Asn
    50                  55                  60 gaa caa tcg att tcc tca ttt tcc gaa gag ctg aag cag tac gga cag    240
Glu Gln Ser Ile Ser Ser Phe Ser Glu Glu Leu Lys Gln Tyr Gly Gln
65                  70                  75                  80 ata gac gtt ctc atc aat aat gca gga acg gca tac ggc gga ttc gct    288
Ile Asp Val Leu Ile Asn Asn Ala Gly Thr Ala Tyr Gly Gly Phe Ala
                85                  90                  95 gaa gag ctt tct ctt ggc gac tac aga aaa cag tat gac acc aat gtt    336
Glu Glu Leu Ser Leu Gly Asp Tyr Arg Lys Gln Tyr Asp Thr Asn Val
            100                 105                 110 ttc ggc ctg gtg gca gtc aca aaa gcg gtc ctt cct tat atg aag aaa    384
Phe Gly Leu Val Ala Val Thr Lys Ala Val Leu Pro Tyr Met Lys Lys
        115                 120                 125 cac agc ggc gcc aaa atc atc aat ctg agc agc atc agc ggg cgg atc    432
His Ser Gly Ala Lys Ile Ile Asn Leu Ser Ser Ile Ser Gly Arg Ile
    130                 135                 140 gct ttc ccc gct ttc tcg gca tat gct tca tca aag cat gca gtt gaa    480
Ala Phe Pro Ala Phe Ser Ala Tyr Ala Ser Ser Lys His Ala Val Glu
145                 150                 155                 160 ggc ttt tca gaa agc ctc cgc ctc gaa ctc cgt cca ttc ggc atc aat    528
Gly Phe Ser Glu Ser Leu Arg Leu Glu Leu Arg Pro Phe Gly Ile Asn
                165                 170                 175 gtg gcc gtc gtc cag ccg gga tcg tac cag acg gcg att tgg gag aca    576
Val Ala Val Val Gln Pro Gly Ser Tyr Gln Thr Ala Ile Trp Glu Thr
            180                 185                 190 tcg ttt gcc gcc caa gtc act gca cct gat gcc gaa tca cag tac aaa    624
Ser Phe Ala Ala Gln Val Thr Ala Pro Asp Ala Glu Ser Gln Tyr Lys
        195                 200                 205 aca tat ttc gag cgg atc tcc gcc tac att gca gcg agc cgc aaa cat    672
Thr Tyr Phe Glu Arg Ile Ser Ala Tyr Ile Ala Ala Ser Arg Lys His
    210                 215                 220 tac gga aac ccg gat gat gtg gct gaa ttg atc tgc cga ctc gct gca    720
Tyr Gly Asn Pro Asp Asp Val Ala Glu Leu Ile Cys Arg Leu Ala Ala
225                 230                 235                 240 aaa aag cgg ctg aac agg ctg cgc tat ccg atc ggc agg ggc gtc cgt    768
```

```
                Lys Lys Arg Leu Asn Arg Leu Arg Tyr Pro Ile Gly Arg Gly Val Arg
                            245                 250                 255 ctc tcg atc ctt ctc cac caa atc ctg cca tgg cgg att tgg gaa cgt                 816
Leu Ser Ile Leu Leu His Gln Ile Leu Pro Trp Arg Ile Trp Glu Arg
                260                 265                 270 gcg gtc ata aaa aaa ttg ctt aaa tga                                             843
Ala Val Ile Lys Lys Leu Leu Lys
                275             280

<210> SEQ ID NO 25
<211> LENGTH: 280
<212> TYPE: PRT
<213> ORGANISM: Bacillus licheniformis SJ1707

<400> SEQUENCE: 25

Leu Asn Asn Lys Ile Ala Ile Val Thr Gly Ala Ser Gly Phe Gly
1               5                   10                  15

Leu Leu Thr Ala Leu Lys Leu Ala Ser Thr His Phe Val Ile Ala Thr
                20                  25                  30

Ala Arg His Pro Glu Lys Ala Glu Ala Leu Arg Asn Arg Ile Ala Glu
            35                  40                  45

Leu Ser Ile Glu Ser Ser Ile Ala Val Ala Glu Leu Asp Val Thr Asn
        50                  55                  60

Glu Gln Ser Ile Ser Ser Phe Ser Glu Leu Lys Gln Tyr Gly Gln
65                  70                  75                  80

Ile Asp Val Leu Ile Asn Asn Ala Gly Thr Ala Tyr Gly Gly Phe Ala
                85                  90                  95

Glu Glu Leu Ser Leu Gly Asp Tyr Arg Lys Gln Tyr Asp Thr Asn Val
            100                 105                 110

Phe Gly Leu Val Ala Val Thr Lys Ala Val Leu Pro Tyr Met Lys Lys
        115                 120                 125

His Ser Gly Ala Lys Ile Ile Asn Leu Ser Ser Ile Ser Gly Arg Ile
130                 135                 140

Ala Phe Pro Ala Phe Ser Ala Tyr Ala Ser Ser Lys His Ala Val Glu
145                 150                 155                 160

Gly Phe Ser Glu Ser Leu Arg Leu Glu Leu Arg Pro Phe Gly Ile Asn
                165                 170                 175

Val Ala Val Val Gln Pro Gly Ser Tyr Gln Thr Ala Ile Trp Glu Thr
            180                 185                 190

Ser Phe Ala Ala Gln Val Thr Ala Pro Asp Ala Glu Ser Gln Tyr Lys
        195                 200                 205

Thr Tyr Phe Glu Arg Ile Ser Ala Tyr Ile Ala Ala Ser Arg Lys His
    210                 215                 220

Tyr Gly Asn Pro Asp Asp Val Ala Glu Leu Ile Cys Arg Leu Ala Ala
225                 230                 235                 240

Lys Lys Arg Leu Asn Arg Leu Arg Tyr Pro Ile Gly Arg Gly Val Arg
                245                 250                 255

Leu Ser Ile Leu Leu His Gln Ile Leu Pro Trp Arg Ile Trp Glu Arg
            260                 265                 270

Ala Val Ile Lys Lys Leu Leu Lys
        275                 280

<210> SEQ ID NO 26
<211> LENGTH: 5313
<212> TYPE: DNA
<213> ORGANISM: artificial sequence
<220> FEATURE:
<223> OTHER INFORMATION: Plasmid pAN212b-yusZ
```

<400> SEQUENCE: 26

```
aattcagatc cttattgttc ccgcggagca gccgttttaa tggaaccgac tccccctctt      60
ccagatatac gcttgatcct tccgtttgag cggcattttt gctgactttc acacgatctt     120
ccaaatttcc gttttctatt gcataaatcg ccgtggcaat tttggttatg ctggctggat     180
acatttttt gcggctgttt ttttcataga ggacctggcc cgatttccca tcgatcaata     240
tagcggaaac gcttttgatt tccggtttgt tttttctcc tgcttgagcc gagctatgaa     300
aaaacagcgt cagacatagt acaataatga acaggaggga tcgtttaaca ttcatcgtgt     360
caccctgcct tctttctctt ttgcaatttt tataaaaata ggtcttttag cactttttaa     420
attttaccaa tgatgaactg tcgctgacaa gccttttctt gtcaacaagc caaaattttg     480
aatggaggaa actcattgaa caataaaatc gcaattgtaa cgggcgcgac gagcatttgg     540
gaacgtgcgg tcataaaaaa attgcttaaa tgaggtaatt taaaataatt ataatttagt     600
attgatttta attttgtatt tgttataata taattaacaa atgaaaaaca cgaggaggaa     660
atatcatatg atctctcaac aattaaaaca gcaaatcct gtacttgaaa actcaatgaa     720
tacgaatttg tcaaactggt tcatcccttta cacgaagctt caccgttttc actggtacgt     780
aaaagggccg cagttctttta ccctacatga aaaatttgaa gagctataca accatgcgtc     840
agaaacagca gatgtgatcg cggaacgctt gctggccatc ggcggacagc cgctcgccac     900
aatgaaagaa tacattgacc acggcacaat tgaggaaaac ggagccgaaa aacggccga     960
agaaatggtt tccgcactgg taagcgattg acgtcgattc acaaaaatag gcacacgaaa    1020
aacaagtaag ggatgcagtt tatgcatccc ttaacttact tattaaataa tttatagcta    1080
ttgaaaagag ataagaattg ttcaaagcta atattgttta aatcgtcaat tcctgcatgt    1140
tttaaggaat tgttaaattg atttttttgta aatatttttct tgtattcttt gttaacccat    1200
ttcataacga ataattata cttttgttta tctttgtgtg atattcttga ttttttttcta    1260
cttaatctga taagtgagct attcacttta ggtttaggat gaaaatattc tcttggaacc    1320
atacttaata tagaaatatc aacttctgcc attaaaagta atgccaatga gcgttttgta    1380
tttaataatc ttttagcaaa cccgtattcc acgattaaat aaatctcatt agctatacta    1440
tcaaaaacaa ttttgcgtat tatatccgta cttatgttat aaggtatatt accatatatt    1500
ttataggatt ggttttttagg aaatttaaac tgcaatatat ccttgtttaa aacttggaaa    1560
ttatcgtgat caacaagttt atttttctgta gttttgcata atttatggtc tatttcaatg    1620
gcagttacga aattacacct ctttactaat tcaagggtaa aatggccttt tcctgagccg    1680
atttcaaaga tattatcatg ttcatttaat cttatatttg tcattatttt atctatatta    1740
tgttttgaag taataaagtt ttgactgtgt tttatatttt tctcgttcat tataaccctc    1800
tttaatttgg ttatatgaat tttgcttatt aacgattcat tataaccact tattttttgt    1860
ttggttgata atgaactgtg ctgattacaa aaatactaaa aatgcccata ttttttcctc    1920
cttataaaat tagtataatt atagcacgag ctctgataaa tatgaacatg atgagtgatc    1980
gttaaattta tactgcaatc ggatgcgatt attgaataaa agatatgaga gatttatcta    2040
atttcttttt tcttgtaaaa aaagaaagtt cttaaaggtt ttatagtttt ggtcgtagag    2100
cacacggttt aacgacttaa ttcgaagta ataagtcta gtgtgttaga ctttatgaaa    2160
tctatatacg tttatatata tttattatcc ggaggtgtag catgtctcat tcaattttga    2220
gggttgccag agtaaagga tcaagtaata caaacgggat acaaagacat aatcaaagag    2280
agaataaaaa ctataataat aaagacataa atcatgagga aacatataaa aattatgatt    2340
```

```
tgattaacgc acaaaatata aagtataaag ataaaattga tgaaacgatt gatgagaatt    2400
attcagggaa acgtaaaatt cggtcagatg caattcgaca tgtggacgga ctggttacaa    2460
gtgataaaga tttctttgat gatttaagcg gagaagaaat agaacgattt tttaaagata    2520
gcttggagtt tctagaaaat gaatacggta aggaaaatat gctgtatgcg actgtccatc    2580
tggatgaaag agtcccacat atgcactttg gttttgtccc tttaacagag gacgggagat    2640
tgtctgcaaa agaacagtta ggcaacaaga aagactttac tcaattacaa gatagattta    2700
atgagtatgt gaatgagaaa ggttatgaac ttgaaagagg cacgtccaaa gaggttacag    2760
aacgagaaca taaagcgatg gatcagtaca agaaagatac tgtatttcat aaacaggaac    2820
tgcaagaagt taaggatgag ttacagaagg caaataagca gttacagagt ggaatagagc    2880
atatgaggtc tacgaaaccc tttgattatg aaaatgagcg tacaggtttg ttctctggac    2940
gtgaagagac tggtagaaag atattaactg ctgatgaatt tgaacgcctg caagaaacaa    3000
tctcttctgc agaacggatt gttgatgatt acgaaaatat taagagcaca gactattaca    3060
cagaaaatca gaattaaaa aaacgtagag agagtttgaa agaagtagtg aatacatgga    3120 aagagggggta tcacgaaaaa agtaaagagg ttaataaatt aaagcgagag aatgatagtt    3180
tgaatgagca gttgaatgta tcagagaaat ttcaagctag tacagtgact ttatatcgtg    3240
ctgcgagggc gaatttccct gggtttgaga aagggtttaa taggcttaaa gagaaattct    3300
ttaatgattc caaatttgag cgtgtgggac agtttatgga tgttgtacag gataatgtcc    3360
agaaggtcga tagaaagcgt gagaaacagc gtacagacga tttagagatg tagaggtact    3420
tttatgccga gaaaactttt tgcgtgtgac agtccttaaa atatacttag agcgtaagcg    3480
aaagtagtag cgacagctat taactttcgg tttcaaagct ctaggatttt taatggacgc    3540
agcgcatcac acgcaaaaag gaaattggaa taaatgcgaa atttgagatg ttaattaaag    3600
acctttttga ggtctttttt tcttagattt ttggggttat ttaggggaga aaacataggg    3660
gggtactacg acctcccccc taggtgtcca ttgtccattg tccaaacaaa taaataaata    3720
ttgggttttt aatgttaaaa ggttgttttt tatgttaaag tgaaaaaaac agatgttggg    3780
aggtacagtg atggttgtag atagaaaaga agagaaaaaa gttgctgtta ctttaagact    3840
tacaacagaa gaaaatgaga tattaaatag aatcaaagaa aaatataata ttagcaaatc    3900
agatgcaacc ggtattctaa taaaaaaata tgcaaaggag gaatacggtg cattttaaac    3960
aaaaaaagat agacagcact ggcatgctgc ctatctatga ctaaattttg ttaagtgtat    4020
tagcaccgtt attatatcat gagcgaaaat gtaataaaag aaactgaaaa caagaaaaat    4080
tcaagaggac gtaattggac atttgtttta tatccagaat cagcaaaagc cgagtggtta    4140
gagtatttaa aagagttaca cattcaattt gtagtgtctc cattacatga tagggatact    4200
gatacagaag gtaggatgaa aaaagagcat tatcatattc tagtgatgta tgagggtaat    4260
aaatcttatg aacagataaa aataattaca gaagaattga atgcgactat tccgcagatt    4320
gcaggaagtg tgaaaggtct tgtgagatat atgcttcaca tggacgatcc taataaattt    4380
aaatatcaaa agaagatat gatagtttat ggcggtgtag atgttgatga attattaaag    4440 aaacaacaa cagatagata taaattaatt aagaaaatga ttgagtttat tgatgaacaa    4500
ggaatcgtag aatttaagag tttaatggat tatgcaatga agtttaaatt tgatgattgg    4560
ttcccgcttt tatgtgataa ctcggcgtat gttattcaag aatatataaa atcaaatcgg    4620
tataaatctg accgatagat tttgaattta ggtgtcacaa gacactcttt tttcgcacca    4680
gcgaaaactg gtttaagccg actgcgcaaa agacataatc gactctagag gatccccggg    4740
```

```
taccgagctc tgcctttag tccagctgat ttcactttt gcattctaca aactgcataa    4800
ctcatatgta aatcgctcct ttttaggtgg cacaaatgtg aggcatttc gctctttccg   4860 gcaaccactt ccaagtaaag tataacacac tatactttat attcataaag tgtgtgctct  4920
gcgaggctgt cggcagtgcc gaccaaaacc ataaaacctt taagaccttt cttttttta   4980 cgagaaaaaa gaaacaaaaa aacctgccct ctgccacctc agcaaagggg ggttttgctc  5040
tcgtgctcgt ttaaaaatca gcaagggaca ggtagtattt tttgagaaga tcactcaaaa  5100
aatctccacc tttaaaccct tgccaattt tattttgtcc gttttgtcta gcttaccgaa   5160
agccagactc agcaagaata aaattttat tgtctttcgg ttttctagtg taacggacaa   5220
aaccactcaa aataaaaaag atacaagaga ggtctctcgt atcttttatt cagcaatcgc  5280
gcccgattgc tgaacagatt aataatgagc tcg                               5313
```